(12) United States Patent
Easterly

(10) Patent No.: US 8,959,012 B2
(45) Date of Patent: Feb. 17, 2015

(54) SYSTEM AND METHOD FOR THE AUTOMATIC GENERATION OF PATIENT-SPECIFIC AND GRAMMATICALLY CORRECT ELECTRONIC MEDICAL RECORDS

(76) Inventor: Orville E. Easterly, Granite Bay, CA (US)

(*) Notice: Subject to any disclaimer, the term of this patent is extended or adjusted under 35 U.S.C. 154(b) by 594 days.

(21) Appl. No.: 13/118,565

(22) Filed: May 30, 2011

(65) Prior Publication Data

US 2011/0231207 A1 Sep. 22, 2011

Related U.S. Application Data

(63) Continuation-in-part of application No. 11/732,604, filed on Apr. 4, 2007, now abandoned.

(51) Int. Cl.
G06F 17/27 (2006.01)
G06F 17/24 (2006.01)
G06F 17/28 (2006.01)
G06Q 50/24 (2012.01)

(52) U.S. Cl.
CPC .......... *G06F 17/248* (2013.01); *G06F 17/2881* (2013.01); *G06Q 50/24* (2013.01)
USPC ..................................... 704/9; 704/1; 704/10

(58) Field of Classification Search
CPC ..... G06F 17/27; G06F 17/20; G06F 17/2705;
G06F 17/271; G06F 17/2715; G06F 17/272;
G06F 17/2725; G06F 17/273; G06F 17/2735;
G06F 17/274; G06F 17/2745; G06F 17/275;
G06F 17/2755; G06F 17/276; G06F 17/2765;
G06F 17/277; G06F 17/2775

USPC .................................................. 704/1, 9, 10
See application file for complete search history.

(56) References Cited

U.S. PATENT DOCUMENTS

| 5,732,221 A | 3/1998 | Feldon et al. |
| 5,802,495 A * | 9/1998 | Goltra ............................ 705/3 |
| 5,909,678 A * | 6/1999 | Bergman et al. ................... 1/1 |

(Continued)

FOREIGN PATENT DOCUMENTS

| KR | 10-1998-0047640 | 6/2000 |
| KR | 10-2002-0051596 | 12/2000 |

(Continued)

OTHER PUBLICATIONS

PCT Patentability Report, Jun. 10, 2009, Easterly.

*Primary Examiner* — Lamont Spooner
(74) *Attorney, Agent, or Firm* — Inventive Patent Law P.C.; Jim H. Salter

(57) ABSTRACT

A system and method for automatically generating patient-specific and grammatically correct electronic medical records is disclosed. The system and method of an example embodiment includes retrieving a statement from a data object, the data object including the statement, at least one response option corresponding to the statement, and at least one sentence fragment corresponding to the response option; generating, using a processor, a user interface view that includes the statement; receiving a response corresponding to the statement; correlating the response to the at least one response option; retrieving the sentence fragment that corresponds to the correlated response option; and generating, using the processor, a patient-specific and grammatically correct electronic medical record using the retrieved sentence fragment.

17 Claims, 43 Drawing Sheets

(56) References Cited

U.S. PATENT DOCUMENTS

| | | |
|---|---|---|
| 6,289,301 B1 * | 9/2001 | Higginbotham et al. ......... 704/1 |
| 6,338,039 B1 | 1/2002 | Lonski et al. |
| 6,581,204 B2 | 6/2003 | DeBusk et al. |
| 6,587,830 B2 | 7/2003 | Singer |
| 6,684,188 B1 | 1/2004 | Mitchell et al. |
| 6,746,399 B2 | 6/2004 | Iliff |
| 6,801,916 B2 | 10/2004 | Roberge et al. |
| 6,826,578 B2 | 11/2004 | Brackett et al. |
| 6,938,203 B1 | 8/2005 | Dimarco et al. |
| 6,988,990 B2 | 1/2006 | Pan et al. |
| 7,008,378 B2 | 3/2006 | Dean |
| 7,020,618 B1 | 3/2006 | Ward |
| 7,133,937 B2 | 11/2006 | Leavitt |
| 7,555,425 B2 * | 6/2009 | Oon ................................. 704/9 |
| 7,774,694 B2 * | 8/2010 | Watson et al. ................ 715/224 |
| 2004/0143689 A1 | 7/2004 | Leavitt |
| 2005/0065423 A1 | 3/2005 | Owen |
| 2005/0086078 A1 | 4/2005 | Maloney et al. |
| 2005/0096910 A1 * | 5/2005 | Watson et al. ................ 704/260 |
| 2005/0197547 A1 * | 9/2005 | Trinks et al. .................. 600/300 |
| 2006/0059012 A1 | 3/2006 | Thompson |
| 2006/0190483 A1 | 8/2006 | Takahashi et al. |
| 2007/0260449 A1 * | 11/2007 | Pan et al. ......................... 704/9 |
| 2008/0021288 A1 * | 1/2008 | Bowman et al. ............... 600/300 |
| 2008/0249761 A1 | 10/2008 | Easterly |

FOREIGN PATENT DOCUMENTS

| | | |
|---|---|---|
| KR | 10-1998-0024120 | 5/2001 |
| KR | 10-1999-0056473 | 8/2001 |
| KR | 10-2000-0031541 | 8/2002 |
| KR | 10-2001-0082493 | 7/2003 |
| WO | WO/2008/123966 A1 | 10/2008 |

* cited by examiner

_____
        310     312                                         305

Initial Consultation

Chief Complaint: otitis media

314

History of Present Illness: Mr. John Jones is a 35 year old Caucasian male who approximately 2 days ago developed the gradual onset of painful otitis media described as constant involving the right ear. The symptoms are persistent and have exacerbated. Additionally, he admits to loss of auditory acuity of the right ear, tinnitus and right auditory canal discharge. The symptoms have been exacerbated self-instrumentation of the auditory canal, wax removal drops and/or irrigation and movement. He has noted relief when lying on his/her right side. He has been taking no medications for this condition.

Review of Systems: General: He admits to fever, chills, malaise, fatigability, but denies night sweats, recent weight gain, recent weight loss, or a history of familial disorders. Head: He denies chronic or recurrent headaches, migraine headaches, a history of major head trauma, recurrent vertigo, recurrent syncope, seizures or pediculosis capitis. Eyes: He denies recent loss of vision, recent inflammation or infection, pain, photophobia, diplopia, visual field loss, a history of color blindness, major eye trauma, glaucoma, cataracts or a history of chloramphenicol exposure. Ears: He/She denies loss of hearing or deafness, ear pain, tinnitus, vertigo, auditory canal discharge, recurrent otitis media, mastoiditis or a history of acoustic neruroma. Nose: He admits to chronic nasal discharge, obstruction, but denies frequent coryza, recurrent or chronic rhinitis, chronic sinusitis, epistaxis or a history of nasal Wegener's granulomatosis. Mouth: He denies soreness of the mouth, the tongue, bleeding gums or sialolithiasis. Throat: He admits to hoarseness, frequent or recurrent sore throats, but denies recurrent tonsillitis, a recent voice change, a history of oropharyngpeal carcinoma or a history of adenoid cystic carcinoma. Neck: He denies swelling, pain, lymph node enlargement, goiter, stiffness, limitation of motion, a history of a thyroglossal duct cyst or a history of a branchial cleft cyst. Respiratory System: He denies pain, shortness of breath, wheezing, dyspnea, proxysmal nocturnal dyspnea, orthopnea, chronic cough, abnormal sputum production, hemoptysis, purulent sputum, night sweats, cyanosis, asthma, emphysema, pleurisy, bronchitis, pneumonia or tuberculosis. Cardiovascular System: He/She denies palpitation, tachycardia, arrhythmias, chest pain, heart murmurs, exertional dyspnea, paroxysmal nocturnal dyspnea, orthopnea, hypertension, cough, cyanosis, changes in skin color, ascites, edema, intermittent claudication, cold extremities, angina, myocardial infarction, congestive heart failure, a history of phlebitis, deep venous thromboses, congenital cardiac anomalies, rheumatic fever, syphilis or diphtheria.
_____

Figure 3

────────────────────────────────────────────── 306
              ┌── 310      ┌── 312
             /            /
            /            /  Initial Consultation
──────────/────────────/──────────────────────────
Chief Complaint: // otitis media//

┌── 314              ┌── 551
History of Present Illness: // Mr. John Jones is a 35 year old Caucasian
                                                     ┌── 552
male who approximately 2 days ago developed // the gradual onset of //
         ┌── 553         ┌── 554              ┌── 555
painful otitis media // described as constant // involving the right ear. // The symptoms are persistent and have exacerbated. // Additionally, he admits to // loss of auditory acuity of the right ear //, // tinnitus //, and // right auditory canal discharge. // The symptoms have been exacerbated by // self-instrumentation of the auditory canal //, // wax removal drops and/or irrigation // , and // with movement. // He has noted relief // when lying on his/her right side. // He has been taking no medications for this condition. //

| Sentence Fragment 1 -551- "Mr. John Jones is a 35 year old Caucasian male who approximately 2 days ago developed" | Sentence Fragment 2 -552- "the gradual onset of" | Sentence Fragment 3 -553- "painful otitis media" | Sentence Fragment 4 -554- "described as constant" | Sentence Fragment 5 -555- "involving the right ear." |
|---|---|---|---|---|

557

// Mr. John Jones is a 35 year old Caucasian male who approximately 2 days ago developed // the gradual onset of // painful otitis media // described as constant // involving the right ear. //

558

Mr. John Jones is a 35 year old Caucasian male who approximately 2 days ago developed the gradual onset of painful otitis media described as constant involving the right ear.

| ID | Instructions Statement | Response Type | # of responses | Responses | # of Sentences | Sentence | Sentence ID | Report Location | Special Instructions |
|---|---|---|---|---|---|---|---|---|---|
| 1 | Please select the one symptom which most accurately applies to you. You will be able to choose only one. You will be able to add any additional symptoms later. | radio | 9 | loss of hearing | 1 | loss of auditory acuity | 7824 | Report: Chief Complaint: | If the patient chooses this option, a window at New Edit of Catagories\History of Present Illness\Ears System\S_Ears_Loss of Hearing.xls opens. |
| | | | | deafness | 1 | deafness | 7824.1 | Report: Chief Complaint: | If the patient chooses this option, a window at New Edit of Catagories\History of Present Illness\Ears System\S_Ears_Deafness.xls opens. |
| | | | | pain in one or both ears | 1 | otalgia | 7825 | Report: Chief Complaint: | If the patient chooses this option, a window at New Edit of Catagories\History of Present Illness\Ears System\S_Ears_Ear Pain.xls opens. |
| | | | | recurrent ringing in one or both ears | 1 | tinnitus | 7826 | Report: Chief Complaint: | If the patient chooses this option, a window at New Edit of Catagories\History of Present Illness\Ears System\S_Ears_Tinnitus.xls opens. |

| 410 | 412 | 414 | 416 | 418 | 420 | 422 | 424 | 426 |
|---|---|---|---|---|---|---|---|---|
| | | | discharge from an ear | 1 | auditory canal discharge | 7828 | Report: Chief Complaint: | If the patient chooses this option, a window at New Edit of Catagories \History of Present Illness\Ears System\S_Ears_Auditory Canal Discharge.xls opens. |
| | | | ear infection | 1 | otitis media | 7829 | Report: Chief Complaint: | If the patient chooses this option, a window at New Edit of Catagories \History of Present Illness\Ears System\S_Ears_Otitis Media.xls opens. |
| | | | recurrent mastoiditis | 1 | mastoiditis | 7830 | Report: Chief Complaint: | If the patient chooses this option, a window at New Edit of Catagories \History of Present Illness\Ears System\S_Ears_Mastoiditis.xls opens. |
| | | | cholesteatoma | 1 | cholesteatoma | 7830.1 | Report: Chief Complaint: | If the patient chooses this option, a window at New Edit of Catagories \History of Present Illness\Ears System\S_Ears_Cholesteatoma.xls opens. |
| | user input | 1 | user input | 1 | "user response" | 7831 | Report: Chief Complaint: | If the patient chooses this option, a window at New Edit of Catagories \History of Present Illness\Ears System\S_Ears_User Response.xls opens. |
| If none of the other symptoms listed above apply to you, please type in the one symptom for which you are to be seen by a physician. Choose only one symptom. You will be able to add any additional symptoms later. | | | | | | | | |
| 428 | | | | | | | | |

[a1] Chief Complaint: General: [7795] recent fevers [7796] chills [7797] malaise [7798] fatigability [7799] weakness [7800] night sweats [7801] weight gain [7802] weight loss [7803] [user response] Head: [7804] chronic or recurrent headaches [7805] migraine headaches [7806] mass on head [7807] history of major head trauma [7808] recurrent vertigo [7809] recurrent syncope [7810] seizures [7811] pediculosis capitis [7812] [user response] Eyes: [7813] loss of vision [7813.1] blindness [7814] ocular inflammation or infection [7815] ocular pain [7816] photophobia [7817] diplopia [7818] visual field loss [7819] color blindness [7819.1] flashing lights [7819.2] excessive tearing [7820] ocular trauma [7821] glaucoma [7822] cataracts [7823] [user response] Ears: [7824] loss of auditory acuity [7824.1] deafness [7825] otalgia [7826] tinnitus [7827] vertigo [7828] auditory canal discharge [7829] otitis media [7830] mastoiditis [7830.1] cholesteatoma [7831] "user response" Nose: [7832] frequent coryza [7833] recurrent or chronic rhinitis [7834] chronic sinusitis [7835] chronic nasal discharge [7836] nasal obstruction [7837] epistaxis [7838] "user response" ...

[a1.1] History of Present Illness: [8069] r1, r1a, r1b is a r9 year old r8 r15/r15a who approximately [user response] developed the [8069.1] r1, r1a, r1b is a r9 year old r8 r15/r15a who was given the diagnosis of diverticulosis/diverticulitis approximately [user response]. [8069.2] r1, r1a, r1b is a r9 year old r8 r15/r15a who was given the diagnosis of gastroesophageal reflux disease approximately [user response]. [8069.3] r1, r1a, r1b is a r9 year old r8 r15/r15a who was given the diagnosis of gallbladder disease approximately [user response]. [8069.4] r1, r1a, r1b is a r9 year old r8 r15/r15a who was given the diagnosis of a pancreatic tumor approximately [user response]. [8069.5] r1, r1a, r1b is a r9 year old r8 r15/r15a who was given the diagnosis of hepatitis approximately [user response]. [8069.6] r1, r1a, r1b is a r9 year old r8 r15/r15a who was given the diagnosis of liver disease approximately [user response]. ...

...[8074] the gradual onset of [8074.1] gradual onset of a change in appetite. [8074.2] gradual onset of fatty food intolerance. [8074.3] gradual onset of nausea with vomiting. [8074.9] gradual onset of nausea without vomiting. [8074.4] bleeding, [8074.5] non-bleeding, [8074.6] pruritic, [8074.7] non-pruritic, [8074.8] gradual onset of nausea with vomiting. [8074.11] gradual onset of rectal/anal pain. [8074.14] gradual onset of a wheat intolerance. ...
[8076] a painful, [8076.64] a painful [8076.1] painful acholic stools. [8076.2] painful constipation. [8076.3] painful ascites. [8076.4] painful diarrhea. [8076.5] painful diverticulitis. [8076.6] painful hemorrhoids. [8076.7] painful rectal bleeding. [8076.8] a painful urine color change. [8076.9] painful urination. [8076.11] painful hesitancy. [8076.13] painful frequency. [8076.14] painful urgency. [8076.15] painful polyuria. [8076.16] painful oliguria. [8076.17] painful nocturia. [8076.18] painful hematuria.... [8076.65] a painful cholesteatoma [8076.66] painful otitis media. [8076.69] [8076.71]...

Figure 9A

...The flashing lights are painful. [8076.58] There has been associated pain [8076.59] described as intermittent. [8076.67] described as intermittent [8076.61] described as constant. [8076.68] described as constant [8076.62] there has been associated pain [8076.63] There has been associated fever. [8076.65] a painful cholesteatoma [8076.66] painful otitis media. [8076.69] [8076.71] [8076.72] [8076.73] [8076.74] [8076.75] [8076.76] [8076.77] [8076.78] [8076.79] [8076.81] [8076.82] [8076.83] [8076.84] [8076.85]...

...[10000] involving the right eye. [10001] involving the left eye. [10002] involving both eyes. [10003] The description is that of a central deficit. [10004] The description is that of a peripheral deficit. [10005] The description is that of a hemianopsia. [10006] The description is that of a quadrantanopsia. [10007onset of an auditory canal discharge involving the right ear. [10008] onset of an auditory canal discharge involving the left ear. [10009] onset of an auditory canal discharge involving both ears. [10010] involving the right nostril. [10011] involving the left nostril. [10012] involving both nostrils. [10013] The discharge has been purulent and [10014] The discharge has been clear and [10015] The discharge has been bloody and [10016] involving the right ear. [10017] involving the left ear. [10018] involving both ears...

...[8124] The symptoms are continuous and remain unchanged. [8124.1] The symptoms are persistent and remain unchanged. [8125] The symptoms, while continuous, have improved. [8125.1] The symptoms, while persistent, have improved. [8126] The symptoms are continuous and have exacerbated. [8126.1] The symptoms are persistent and have exacerbated. ...

...[8082] Additionally, he/she admits to [8082.1] He/She admits to [8083] He/She has identified no associated complaints. [8084] a change in appetite, [8085] wheat intolerance, [8086] fatty food intolerance, [8087] lactose intolerance, [8088] fever, [8088.1] change in color of urine, [8088.2] dysuria, [8088.3] hesitancy, [8088.4] frequency, [8088.5] urgency, [8088.6] polyuria, [8088.7] oliguria, [8088.8] nocturia, [8088.9] hematuria, [8088.11] pyuria, [8088.12] urinary retention, [8088.13] urinary straining, [8088.14] incontinence, [8088.15] renal pain or colic, ...

...[8423] color blindness [8423.1] flashing lights [8423.2] floaters [8423.3] excessive tearing of the right eye [8423.4] excessive tearing of the left eye [8423.5] excessive tearing bilaterally [8424] right ocular trauma [8424.1] left ocular trauma [8424.2] bilateral ocular trauma [8425] glaucoma [8426] cataracts [8427] "user response" [8428] loss of auditory acuity of the right ear [8428.1] loss of auditory acuity of the left ear [8428.2] bilateral loss of auditory acuity [8428.3] deafness of the right ear [8428.4] deafness of the left ear [8428.5] bilateral deafness [8429] otalgia of the right ear [8429.1] otalgia of the left ear [8429.2] bilateral otalgia [8430] tinnitus [8431] vertigo [8432] right auditory canal discharge [8432.1] left auditory canal discharge [8432.2]...

... [8151] The symptoms have been exacerbated by [user response]. [8152] There have been no exacerbating factors. ...

⎯⎯⎯⎯ 812

... [9000] intense ambient light [9001] low ambient light [9002] hyperglycemia [9003] close work [9004] reading [9005] distance [9006] headaches [9007] migraine [9008] allergic reactions [9009] chemical exposure [9010] sleep deprivation [9010.1] fatigue [9011] [user input] [9012] proprietary medications [9013] proprietary ear drops [9014] self-instrumentation of the auditory canal [9015] foreign bodies in the auditory canal [9016] wax removal drops and/or irrigation [9017] intense sounds [9018] low volume sounds [9019] high ambient noise levels [9020] water in the auditory canal [9021] [9022] [9023] ...

⎯⎯⎯⎯ 814

⎯⎯⎯⎯ 816

... [8177.1] with a high residue diet, [8177.2] with a low residue diet, [8178] after avoidance of oral intake, [8179] with movement, [8179.1] with avoidance of movement, [8180] with exercise, [8181] with avoidance of exercise, [8182] when sitting, [8183] when standing, [8184] when lying on his/her back, [8185] when lying on his/her right side, [8186] when lying on his/her left side, [8187] when lying on his/her stomach, [8188] by [user input], ...

⎯⎯⎯⎯ 818

...[8170] He/She has noted relief [user response]. [8171] He/She has identified no remitting factors. [8172] with avoidance of fatty foods, [8173] with avoidance of spicy foods, [8174] with avoidance of milk products, [8174.1] with avoidance of alcohol, [8174.2] with liquid intake, [8174.3] with avoidance of liquids, [8175] after drinking milk, [8176] with avoidance of wheat products, [8176.1] with a high residue diet, [8176.2] with a low residue diet, [8176.3] with avoidance of tomato products, [8177] after any oral intake, [8177.1] with a high residue diet, [8177.2] with a low residue diet, [8178] after avoidance of oral intake, [8179] with movement, [8179.1] with avoidance of movement, [8180] with exercise, [8181] with avoidance of exercise, [8182] when sitting, [8183] when standing, [8184] when lying on his/her back, [8185] when lying on his/her right side, [8186] when lying on his/her left side, [8187] when lying on his/her stomach, [8188] by [user input], ...

⎯⎯⎯⎯ 820

⎯⎯⎯⎯ 822

... [8190] He/She has been taking no medications for this condition. [8191] He/She has been taking [user response] for this condition, [8192] and feels that the symptoms are improved. [8193] and feels that the symptoms are unchanged. [8194] and feels that the symptoms have exacerbated in spite of the medication. [8195] and feels that the symptoms have been exacerbated by the medication. ...

| ID | Instructions | Statement | Response Type (452) | # of responses (454) | Responses (456) | # of Sentences (458) | Sentence (460) | Sentence ID (462) | Report Location (464) | Special Instructions (466) |
|---|---|---|---|---|---|---|---|---|---|---|
| | Your physician's office or the person who is doing your pre-surgery psycyological assessment gave you an access code when they told you to register at this site. Please enter that number into the space provided. | Please enter the access code here. | user input | 1 | user input | 0 | | | Physician's website | The access code will be entered on the home page of the physician's or mental health professional's website. After the patient enters the access code, the registration form opens where the patient will click on their |
| | Please provide each of the items requested on the registration form. The items in Red are required. You will not be able to proceed until this information is entered correctly. | First name, Middle name or initial, Last name | name field | 1 | user input | 10 | Mr./Ms. [first name] [middle initial or name] [last name] | r1, r1a, r1b | Report: demographic page under title of the report following Patient: Mr./Ms. | The following number/letter combinations indicate the place marker for first, middle, and last name. [r1] first name, [r1a] middle name, [r1b] last name. The prefix of Mr., Ms. and |
| | | | | | | | Mr./Ms. [first name] [middle initial or name] [last name] | r1, r1a, r1b | Report: demographic page, first line of table following | |
| | | | | | | | Mr./Ms. [first name] [middle initial or name] [last name] | r1, r1a, r1b | Report: First page of the report, first line following a1.1, b1.1, and c1.1. | |
| | | | | | | | Mr./Ms. [last name] | r1c | Report: body of the report. | |

Figure 10B

| 450 | 452 | 454 | 456 | 458 | 460 | 462 | 464 | 466 |
|---|---|---|---|---|---|---|---|---|
| Home phone number | phone number field | 1 | user input | 2 | [response] | r17 | Report: demographic page in the table. | All phone numbers must be preceded by the area code. |
| | | | | | Home Phone: | r33 | Report: demographic page in the table. | |
| Work phone number | phone number field | 1 | user input | 2 | [response] | r18 | Report: demographic page in the table. | |
| | | | | | Work Phone: | r34 | Report: demographic page in the table. | |
| Cell phone number | phone number field | 1 | user input | 2 | [response] | r19 | Report: demographic page in the table. | |
| | | | | | Cell Phone: | r35 | Report: demographic page in the table. | |
| Email address | email field | 1 | user input | 2 | [response] | r20 | Report: demographic page in the table. | |
| | | | | | Email: | r36 | Report: demographic page in the table. | |
| Gender | radio | 2 | Male | 2 | Male | r15 | Report: demographic page, first line of the table after the word Gender: | Be certain that the correct adjustment for gender is made through out the report such as male, female, Mr. or Ms., he or she, him or her, etc. |

Figure 10C

| 450 | 452 | 454 | 456 | 458 | 460 | 462 | 464 | 466 |
|---|---|---|---|---|---|---|---|---|
| Age | age field | 1-110 | radio | 4 | [user response] | r9 | Report: Demographic table | |
| | | | | | [user response] | r9a | Report: First page. | |
| | | | | | [user response] | r9a | Report: First page. | |
| | | | | | Age: | r28 | Report: Demographic table | |
| Date of Birth | Date of Birth field | 1 | radio | 2 | [user response] | r10 | Report: Demographic table | |
| | | | | | Date of Birth: | r29 | Report: Demographic table | |
| Race | race field | 18 | radio | 4 | [user response] | r8 | Report: Demographic table | Race List.doc |
| | | | | | Race: | r27 | Report: Demographic table | |
| | | | | | [user response] | r8a | Report: First page. | |
| | | | | | [user response] | r8a | Report: First page. | |
| Height | height field | height scale | radio | 2 | [user response] | r11 | Report: Demographic table | |
| | | | | | Height: | r30 | Report: Demographic table | |
| Current weight | weight field | 1-999 | radio | 17 | [user response] | r12 | Report: Demographic table | |
| | | | | | Current Weight: | r31 | Report: Demographic table | |

| ID | Instructions | Statement | Response Type | # of responses | Responses | # of Sentences | Sentence | Sentence ID | Report Location | Special Instructions to Programmer |
|---|---|---|---|---|---|---|---|---|---|---|
| | | 431 | 432 | 434 | 436 | 438 | 440 | 442 | 444 | 446 |
| 445 | Please respond to each of the following statements concerning your single, most important symptom (the reason for which you are being seen by a physician). You must be as accurate as possible in your responses in order for your physician to adequately evaluate and treat you.<br><br>Select the one response from the five (5) options which most accurately describes when your medical problem FIRST started. It is vital that you indicate the very first time you noticed this problem no matter how minor it seemed at the time. You will be able to choose only one. | I FIRST experienced an ear infection approximately | radio | 5 | 1-24 hours ago | 1 | r1, r1a, r1b is a r9 year old r8 r15/r15a who approximately [user response] developed the | 8069 | Report: History of Present Illness: | The time-span goes into the [user response] and the sentence goes into the report at 8069. The same for each of the following. |
| | | | | | 2-14 days ago | 1 | r1, r1a, r1b is a r9 year old r8 r15/r15a who approximately [user response] developed the | 8070 | Report: History of Present Illness: | |
| | | | | | 2-4 weeks ago | 1 | r1, r1a, r1b is a r9 year old r8 r15/r15a who approximately [user response] developed the | 8071 | Report: History of Present Illness: | |

Figure 11B

| 430 | 431 | 432 | 434 | 436 | 438 | 440 | 442 | 444 | 446 |
|---|---|---|---|---|---|---|---|---|---|
|  |  |  |  | 1-12 months ago | 1 | r1, r1a, r1b is a r9 year old r8 r15/r15a who approximately [user response] developed the | 8072 | Report: History of Present Illness: |  |
|  |  |  |  | 1-30 years ago | 1 | r1, r1a, r1b is a r9 year old r8 r15/r15a who approximately [user response] | 8073 | Report: History of Present Illness: |  |
| 447 Complete the following sentence by selecting either gradual or rapid in order to indicate how fast the symptom developed. | The ear infection developed | radio | 2 | gradually. | 1 | the gradual onset of | 8074 | Report: History of Present Illness: |  |
|  |  |  |  | rapidly. | 1 | rapid onset of | 8075 | Report: History of Present Illness: |  |
| 448 Please choose one of the options. | The ear infection is | radio | 2 | painful. | 1 | painful otitis media | 8076.66 | Report: History of Present Illness: | If the patient selects painful, a window at New Edit of Catagories \Generic Files Other Systems\Pain Intermittent or Constant No Period.xls opens |
|  |  |  |  | painless. | 1 | painless otitis media | 8078.27 | Report: History of Present Illness: |  |

Figure 11C

| 430 | 431 | 432 | 434 | 436 | 438 | 440 | 442 | 444 | 446 |
|---|---|---|---|---|---|---|---|---|---|
| Complete the following sentence by selecting either intermittent (comes and goes) or constant (always present). | The pain has been | radio | 2 | intermittent (comes and goes) | 1 | described as intermittent | 8076.67 | Report: History of Present Illness: | |
| 449 | | | | constant (always present) | 1 | described as constant | 8076.68 | Report: History of Present Illness: | |
| 451 Please carefully read each of the following statements and select the one which is most accurate. | The ear infection is in | radio | 3 | my right ear. | 1 | involving the right ear. | 10016 | Report: History of Present Illness: | |
| | | | | my left ear. | 1 | involving the left ear. | 10017 | Report: History of Present Illness: | |
| | | | | both ears. | 1 | involving both ears. | 10018 | Report: History of Present Illness: | |
| 455 | Please select the statement which most accurately describes your persistent or continuous symptoms. You | radio | 3 | My persistent symptoms remain unchanged. | 1 | The symptoms are persistent and remain unchanged. | 8124.1 | Report: History of Present Illness: | |
| | | | | My persistent symptoms have improved. | 1 | The symptoms, while persistent, have improved. | 8125.1 | Report: History of Present Illness: | |
| 453 | | | | My persistent symptoms have worsened | 1 | The symptoms are persistent and have exacerbated | 8126.1 | Report: History of Present Illness: | |

Figure 11D

| 430 | 431 | 432 | 434 | 436 | 438 | 440 | 442 | 444 | 446 |
|---|---|---|---|---|---|---|---|---|---|
| 457 | Earlier, you were told that it was necessary to determine the single most important symptom (medical problem) for which you wish to be seen by a physician, and that later you would be able to select all of the symptoms which apply to you.<br><br>In this section, you will be able to choose those additional symptoms, if any.<br><br>First, however, you must answer True or False to the following statement. | In addition to my primary complaint, I have also experienced other symptoms. | combo | 2 | TRUE | 1 | Additionally, he/she admits to | 8082 | Report: History of Present Illness. | 1. If the patient selects True, a window at New Edit of Categories\History of Present Illness\Ear System\Additional Symptoms_Otitis Media.xls opens.<br><br>2. In all cases where I use a list of issues after a statement such as the one that introduces this series, the final choice must insert the conjunction "and" before the final word and a period after the final word. For example, "Additionally, he/she admits |
| | | | | FALSE | 1 | He/She has identified no associated complaints. | 8083 | Report: History of Present Illness: | |

Figure 11E

| 430 | 431 | 432 | 434 | 436 | 438 | 440 | 442 | 444 | 446 |
|---|---|---|---|---|---|---|---|---|---|
| 459 There may be factors which cause your medical problem to become worse.<br><br>Please answer True or False to the following statement. | There are factors which cause my medical problem to worsen. | combo | 2 | TRUE | 1 | The symptoms have been exacerbated by [user response]. | 8151 | | If the patient selects True, a window at New Edit of Categories\History of Present Illness\Ears\Symptoms Worsen_Ears.x is opens<br><br>In all cases where I use a list of issues after a statement such as the one that introduces this series, the final choice must insert the conjunction "and" before the final word and a period after the final word. For example, "Additionally, he/she admits to a change in appetite, wheat |
| | | | | | | | | Report: History of Present Illness: | |
| | | | | FALSE | 1 | There have been no exacerbating factors. | 8152 | | |

Figure 11F

| 430 | 431 | 432 | 434 | 436 | 438 | 440 | 442 | 444 | 446 |
|---|---|---|---|---|---|---|---|---|---|
| There may be factors which cause your symptoms to improve. Please answer True or False to the following statement. | There are factors which cause my symptoms to improve. | combo | | TRUE | 1 | He/She has noted relief [user response]. | 8170 | Report: History of Present Illness: | If the patient selects True, a window at New Edit of Categories\History of Present Illness\Ears\Symptoms_Improve_Ears.xls opens. In all cases where I use a list of issues after a statement such as the one that introduces this series, the final choice must insert the conjunction "and" before the final word and a period after the final word. For example, "Additionally, he/she admits to a change in appetite, wheat |
| | | | | FALSE | 1 | He/She has identified no remitting factors. | 8171 | Report: History of Present Illness: | |

Figure 11G

| 430 | 431 | 432 | 434 | 436 | 438 | 440 | 442 | 444 | 446 |
|---|---|---|---|---|---|---|---|---|---|
| Please select True or False after reading the following statement. | I am taking medication(s) for this condition. | combo | 2 | TRUE | 0 | | | | If the patient selects True, a window at New Edit of Categories\Generic Files\Medication Form and Statements.xls opens. |
| | | | | FALSE | 1 | He/She has been taking no medications for this condition. | 8190 | Report: History of Present Illness. | |
| | I have been seen previously by a physician for this condition. | combo | 2 | TRUE | 0 | | | | If the patient selects True, a window at New Edit of Categories\Generic Files\Previous Physician Form.xls opens. |
| Please select True or False. | | | | FALSE | 1 | The patient has not been seen previously by a physician | 8243 | Report: History of Present Illness. | |

Figure 14

| 430 | 431 | 432 | 434 | 436 | 438 | 440 | 442 | 444 | 446 |
|---|---|---|---|---|---|---|---|---|---|
| ID Instructions | Statement | Response Type | # of responses | Responses | # of Sentences | Sentence | Sentence ID | Report Location | Special Instructions to Programmer |
| 461 Please select the additional symptoms which you have experienced. | I have experienced the following symptoms in addition to my primary problem: | check mark | 15 | loss of hearing in my right ear | 1 | loss of auditory acuity of the right ear | 8428 | Report: History of Present Illness: | In all cases where I use a list of issues after a statement such as the one that introduces this series, the final choice must insert the conjunction "and" before the final word and a |
| | | | | loss of hearing in my left ear | 1 | loss of auditory acuity of the left ear | 8428.1 | Report: History of Present Illness: | |
| | | | | loss of hearing in both ears | 1 | bilateral loss of auditory acuity | 8428.2 | Report: History of Present Illness: | |
| | | | | deafness in my right ear | 1 | deafness of the right ear | 8428.3 | Report: History of Present Illness: | |
| | | | | deafness in my left ear | 1 | deafness of the left ear | 8428.4 | Report: History of Present Illness: | |
| | | | | deafness in both ears | 1 | bilateral deafness | 8428.5 | Report: History of Present Illness: | |
| 463 | | | | recurrent ringing in the ears | 1 | tinnitus | 8430 | Report: History of Present Illness: | |
| | | | | recurrent dizziness | 1 | vertigo | 8431 | Report: History of Present Illness: | |
| 465 | | | | discharge from my right ear | 1 | right auditory canal discharge | 8432 | Report: History of Present Illness: | |
| | | | | discharge from my left ear | 1 | left auditory canal discharge | 8432.1 | Report: History of Present Illness: | |

| Sentence Fragment 11 -576- "The symptoms have been exacerbated by" | Sentence Fragment 12 -577- "self-instrumentation of the auditory canal" | Auto-Fill Text -583- ", " | Sentence Fragment 13 -578- "wax removal drops and/or irrigation" | Auto-Fill Text -584- ", and" | Sentence Fragment 14 -579- "with movement." |
|---|---|---|---|---|---|

580

// The symptoms have been exacerbated by // self-instrumentation of the auditory canal //, // wax removal drops and/or irrigation // , and // with movement.

581

The symptoms have been exacerbated by self-instrumentation of the auditory canal, wax removal drops and/or irrigation, and with movement.

```
                                    ┌─ 587
                ┌──────────┬──────────┐
                │          │ Sentence │
                │ Sentence │Fragment 16│
                │Fragment 15│  -586-  │
                │  -585-   │  "when   │
                │ "He has  │ lying on │
                │noted relief"│ his/her│
                │          │right side."│
                └──────────┴──────────┘
                _____/
                         ∨                    ┌─ 588
// He has noted relief // when lying on his/her right side. //
                _____/
                         ∨                    ┌─ 589

He has noted relief when lying on his/her right side.
```

Figure 19

MDInterview.com — Comprehensive, Accurate, Secure Computer-Patient Interview Instructions: Please complete the following statement by selecting the response or responses which best describe the conditions under which you tend to eat.

You may select <u>more than one</u>

If none of the responses apply to you, please select "<u>None of the above apply to me.</u>"

I tend to:

- ☑ eat when I am bored
- ☑ binge by eating a lot of food during a brief time period
- ☑ keep food hidden at home or at work so that I can eat throughout the day without being discovered
- ☐ eat when I know that no one else is around or that no one else can see me
- ☐ eat until I am so full that I am uncomfortable
- ☐ feel depressed, disgusted, and guilty when I overeat
- ☐ None of the above apply to me

[Back] [Next] [Save/Exit]

Figure 26

| Choices | responses | sentence | posit |
|---|---|---|---|
| auto-populate | eat when I am bored | when #{he/she} is bored | when bored |
| | Text presented as a selectable choice to patient | Text aggregated and outputed to report if choice is selected | |
| | binge by eating a lot of food during a brief time period | in binges | in binges |
| | keep food hidden at home or at work so that I can eat throughout the day without | surreptitiously | surreptitiou |

Figure 30

Pre-Bariatric Surgical Nutritional Evaluation

Purpose of Evaluation: Nutritional evaluation and readiness evaluation in preparation for bariatric procedure

History of Present Illness: nick vangseng is a 27 year old marginally obese Asian male with a BMI of 27.5, who was referred for a pre-surgical nutritional evaluation in consideration of bariatric surgery.

Weight History: As a child, he was first noted to be overweight at the age of 1, although he neither dieted nor exercised in an effort to control his weight. He was of normal weight as an adolescent and did not diet or exercise. He feels that he is currently 30 pounds overweight however he neither diets nor exercises. During the past year, his weight has increased by approximately 10 pounds. He describes feeling his best at the age of 24, at which time he weighed approximately 125 pounds.

Eating Patterns: He alleges to eat three meals per day; that his meals consist of medium portions and; that they are composed primarily of foods which he considers to be "unhealthy" and high in fat, sugar and salt content. He routinely skips breakfast. His average eating habits include restaurant meals 3 times per week, fast foods 3 times per week, fried foods 4 times per week, sweets 6 times per week and non-dietetic, non-alcoholic beverages 8 per week. He identifies, as a regular part of his diet, breakfast cereals, bread and rice. He denies "snacking" between meals. Stressful situations do not appear to dictate his dietary patterns. Additionally, he tends to eat when he is bored, in binges, surreptitiously and when he is unobserved.   ← Response from patient

Commercial Weight Loss Programs: He denies participation in any commercial weight loss programs.

Family History of Obesity: He is unable to provide medical information regarding his biological family members.

Attempts at Non-Surgical Weight Loss: He has no history of sustained attempts at non-surgical weight loss.

Allergies: He describes no medication allergy history. There is a no history of environmental or non-medication allergies.

Past Medical History:
Surgery: None
Trauma: None
Illnesses: None

Vitamins and Supplements: He does not routinely take vitamin/mineral supplements, herbal supplements or protein supplements.

Commitment to Postoperative Regimen: He is not committed to follow the prescribed regimen consisting of diet, exercise and coaching, which will be required following bariatric surgery.

Patient Expectations: He describes no post-bariatric surgery expectations.

Patient Prediction of Outcome: He feels that he is unable to predict the reduction in his excess weight which may potentially result from surgery, and to maintain his weight indefinitely.

Postoperative Support: He lives alone. Arrangements for postoperative care, assistance and nutritional support have not been made at this time.

Figure 31

Eating Patterns: He alleges to eat three meals per day; that his meals consist of medium portions and; that they are composed primarily of foods which he considers to be "unhealthy" and high in fat, sugar and salt content. He routinely skips breakfast. His average eating habits include restaurant meals 3 times per week, fast foods 3 times per week, fried foods 4 times per week, sweets 6 times per week and non-dietetic, non-alcoholic beverages 8 per week. He identifies, as a regular part of his diet, breakfast cereals, bread and rice. He denies "snacking" between meals. Stressful situations do not appear to dictate his dietary patterns. Additionally, he tends to eat when he is bored, in binges, surreptitiously and when he is unobserved.

Commercial Weight Loss Programs: He denies participation in any commercial weight loss programs.

*Response from patient*

Figure 32

SYSTEM AND METHOD FOR THE AUTOMATIC GENERATION OF PATIENT-SPECIFIC AND GRAMMATICALLY CORRECT ELECTRONIC MEDICAL RECORDS

PRIORITY APPLICATION

This is a continuation-in-part patent application of patent application, Ser. No. 11/732,604; filed Apr. 4, 2007 now abandoned by the same applicant. This present patent application draws priority from the referenced co-pending patent application. The entire disclosure of the referenced co-pending patent application is considered part of the disclosure of the present application and is hereby incorporated by reference herein in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2006-2011, Orville Easterly. All Rights Reserved.

BACKGROUND

1. Technical Field

Embodiments relate to the field of data processing. Specifically, various embodiments relate to data processing for electronic medical records.

2. Related Art

Internet research reveals that other companies and organizations, beginning with Mayo Clinic in 1968, have attempted to design and build a computer-patient interview software application that would produce a chart ready patient medical history. To date, these attempts have fallen short of the quality required in order to be accepted across the medical community. There are at least five companies on the Internet that claim to have some form of a computer-patient interview application. The technology offered by each of these companies is described below.

PrimetimeMedical Software in Columbia, S.C. (www.medicalhistory.com) describes their computer-patient interview software as follows; "Branching logic enables patients to progress quickly through adjustable questionnaires from an extensive medical knowledgebase. Sophisticated technology enables this information to transfer to Electronic Medical Records (EMR's). Physician productivity increases because as much as sixty percent of the medical data necessary to complete the visit note can be provided by patients and automatically documented in medical terminology through the Internet, in exam rooms, or in waiting areas before the encounter." PrimetimeMedical Software technology uses "adjustable questionnaires" similar to the questionnaires that the patient currently completes in the physician's waiting room. The physician must then interview the patient to obtain the additional forty percent of the medical data necessary to write or dictate the chart note for that visit.

Kryptiq (www.kryptiq.com) markets a computer-patient interview technology called, CareCatalyst™ Patient Portal. Their web site states that their Patient Portal allows patients to directly input patient information into their physician's Electronic Health Record (EHR) with customizable eForms over the web and to request prescription refills/renewals and appointments online.

RelayHealth (www.relayhealth.com) markets a product called a webvisit. This is an online consultation that is routed directly to a doctor or to his nurse and to which the doctor can then respond. The consultation adapts to the patient's responses; so if a patient answers a question a certain way, his next questions may reflect his previous answer. RelayHealth's webvisit technology is basically email interaction with the patient's physician.

MedicalNetSystems (www.medicalnetsystems.com/) website explains that their TurboHX collects the patient's history in two phases, the patient generated medical history (PGMH) and the physician's editing. "In the PGMH module, the patient develops his or her medical history. The health care provider reviews and edits the patient's history through TURBOHX's edit module." MedicalNetSystems' product does not produce a chart ready comprehensive patient medical history that is professionally written in the vocabulary and syntax of a physician. Their TURBOHX product requires that the physician edit the patient's data entry and put it in chart ready content and format.

Thus, a system and method for automatically generating grammatically correct electronic medical records is needed.

BRIEF DESCRIPTION OF THE DRAWINGS

Embodiments are illustrated by way of example and not limitation in the figures of the accompanying drawings, in which:

FIG. 3 is a diagram illustrating an example of a comprehensive, "patient specific" medical history or initial consultation report in an example embodiment;

FIG. 5 illustrates the history section of an example report extract as partitioned into sentence fragments;

FIG. 7 is a detail of the sentence fragments for a particular example;

FIGS. 8A and 8B are examples of a sample spreadsheet illustrating an example of an input template in one embodiment;

FIGS. 9A, 9B, and 9C are examples of an extract of an output template in one embodiment;

FIGS. 10A-10C and 11A-11G are examples of an input template for the example of one embodiment;

FIG. 14 is an example of an input template for the example of one embodiment;

FIG. 17 is a detail of the sentence fragments for a particular example;

FIG. 19 is a detail of the sentence fragments for a particular example;

FIG. 26 illustrates a particular example of a screenshot of a user interface display or view for a user/patient at the Patient site as generated by the Statement Builder;

FIGS. 27 through 30 illustrate particular examples of screenshots of user interface data displays or views for a host administrator at a Back Office site, generated by the Statement Builder, in which a host administrator can configure Statement Sets, Statement Set Proxies, Statements, and a set of control options to manipulate the behavior and operation of the web application;

FIGS. 31 and 32 illustrate an automatically generated patient-specific and grammatically correct electronic medical record (EMR), which includes a set of patient-specific and grammatically correct sentences generated by the Report Builder based on the configured Statement Sets, Statement Set Proxies, Statements, the set of control options, and the data input by the patient.

DETAILED DESCRIPTION

A system and method for automatically generating patient-specific and grammatically correct electronic medical records is disclosed. In the following description, numerous specific details are set forth. However, it is understood that embodiments of the various embodiments may be practiced without these specific details. In other instances, well-known processes, structures and techniques have not been shown in detail in order not to obscure the understanding of this description.

The various example embodiments described herein provide a capability for automatically generating patient-specific and grammatically correct electronic medical records. In particular, various embodiments provide a system and method for leading a patient through an interview which produces a comprehensive, "patient specific" medical history, which is professionally written in the vocabulary and syntax of physicians. The resultant history is "chart ready" and capable of being downloaded to the physician's computer prior to the actual evaluation. The history can then be amended, edited and expanded by the physician as needed. Additionally, once the physical examination is complete the results of that examination are added. The history and physical examination then become part of the patient's permanent medical record.

The system of an example embodiment includes an input component to receive an input from a user, to map the input to a corresponding sentence fragment, and to retrieve a sentence identifier corresponding to the input. The system further includes an output component to locate the sentence identifier in an output template, and to insert the sentence fragment in the output template at a location indicated by the sentence identifier. Further details in an example embodiment are provided below.

Figure 1:
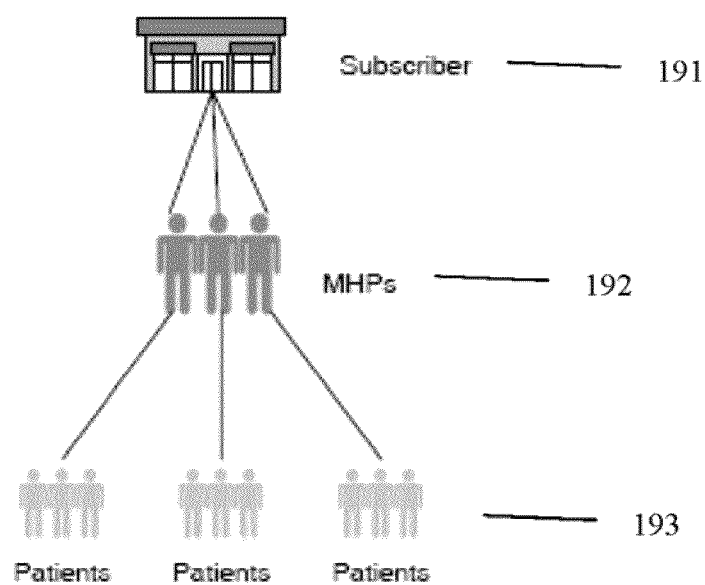
FIG. 1 illustrates an example implementation of the system and method of an example embodiment.

Referring to FIG. 1, an example embodiment of the system and method of an example embodiment is illustrated. In one embodiment, a web-based interface and online application is used by a patient for the input of information related to the patient's medical condition. The web site and online application may be targeted to physicians, surgeons and mental health professionals to assist them in producing a patient's medical and mental health history.

Currently, medical and mental health professionals (MHPs) interview patients and then manually create a medical or mental health history, a time-consuming and costly process. In essence, the web-based interface and online application of a particular embodiment replaces this conventional process by allowing patients to visit the inventive web site to complete an online computer-patient interview.

The web-based interface and online application of a particular embodiment captures patient responses to a series of statements and then produces a comprehensive "chart ready" medical or mental health history or record based on those responses as will be described in more detail below. Note that the medical record generation technology described herein can be applied to the generation of medical, surgical, hospital, mental health, counseling, coaching, physical therapy, mental therapy, behavioral therapy records, or other similar types of medically-related records and documents. The term, "medical record" as used herein includes all forms of these medically-related records. The web-based interface and online application of various embodiments differs from conventional online computer-patient interview software in that the "chart ready" report is "patient specific" and written in complete sentences in the vocabulary and syntax of a dictating physician. The reports of other conventional computer-patient interview software are "patient generic" using one word or incomplete sentences that do not identify the unique medical experience of the patient, but rather applies to any patient selecting the same response or series of responses. The "chart ready" and "patient specific" report of particular embodiments is the real end product of the web site and online application.

Subscriber: Referring to FIG. 1, a subscriber 191 will register with the web site of a particular embodiment and purchase a subscription to the software of a particular embodiment from an online e-commerce store, agree to the user license, edit subscriber information and access and print reports generated by the online software. In addition, subscribers will also be able to download patient medical and mental health histories to their local computer in a conventional CSV file format. Some subscribers will have multiple MHPs 192 within their organization. Subscriber will be able to input MHP personal contact information and the application will assign a unique identifier to each MHP 192.

MHP: Medical or mental health professionals 192 are members of the professional staff in the subscribers' offices. MHPs will be provided with a unique identifier within the online database.

Patient: The patient 193 is the true end-user of the online application of various embodiments. The patients 193 may fill in personal contact and demographic information and respond to a series of medically-related statements and questions. Patients will be provided a unique identifier from the MHP 192, and will be asked to create a username and password to access the system. By entering the identifier received from the MHP 192, the MHP's information can be inserted into the final report. By entering the username/password, the patient 193 can "save" progress in the entry of the patient's medical information, exit the system and return later to complete the questionnaire. In addition, once the patient 193 completes the questionnaire and confirms completion, the unique username/password assigned to the patient 193 will be "locked," disallowing the patient 193 to revisit the questionnaire without a new username and password being created.

Definition of Patient Specific: The medical history report automatically created by particular embodiments described herein is written specifically about the patient who completes the online computer-patient interview, in the vocabulary and syntax of a dictating physician, using complete grammatically-correct sentences with adjectives and adverbs which describe the patient's unique medical experience and/or condition. Lists are used when appropriate to present certain behaviors and symptoms that are unique to the patient.

Figure 2:
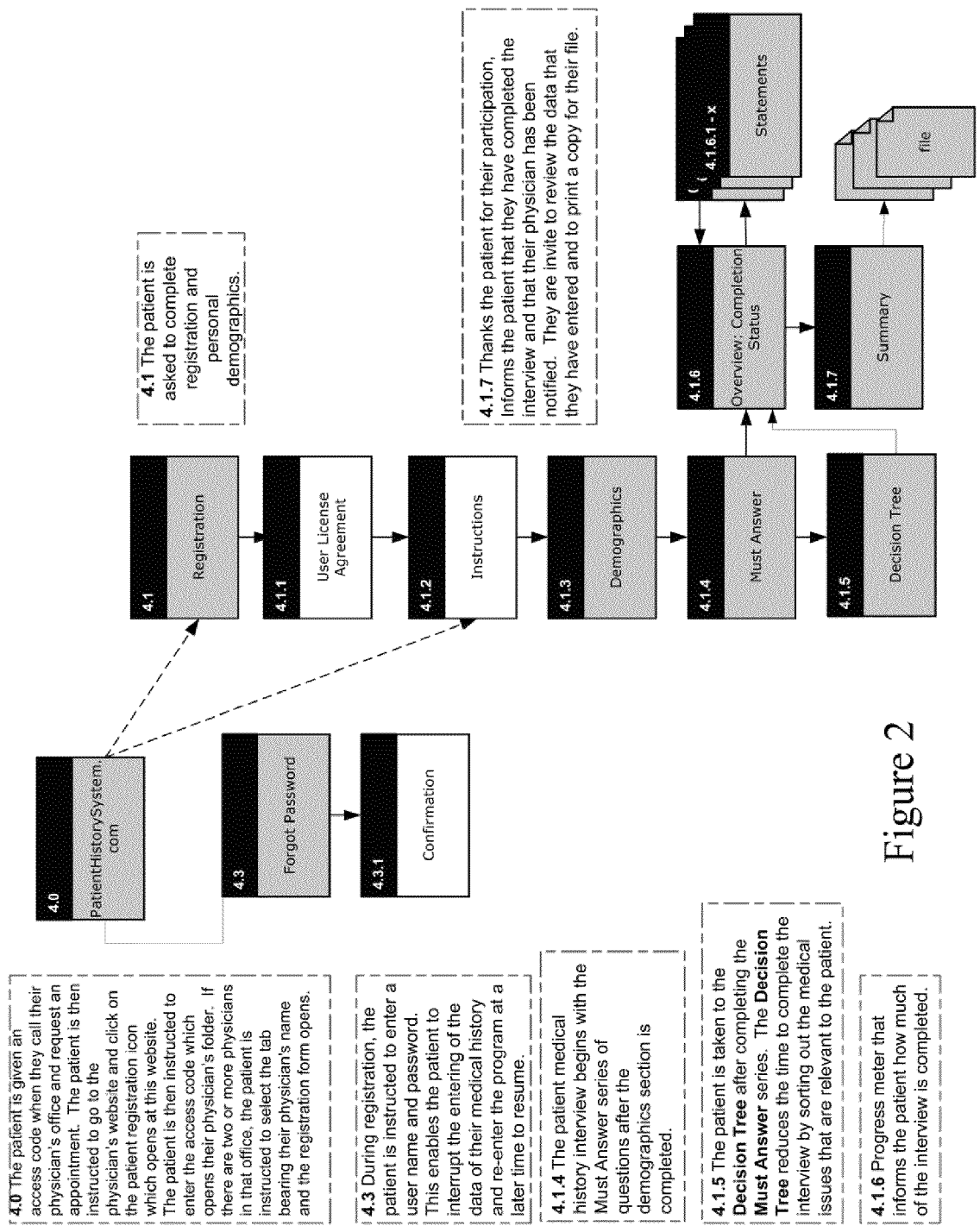
FIG. 2 is an operational flow diagram illustrating a series of steps in using an example embodiment.

Referring to FIG. 2, an operational flow diagram illustrates a series of steps in using an example embodiment. Initially in step 4.0, the patient is given an access code when they call their physician's office and request an appointment. The patient is then instructed to go to the physician's website and click on the patient registration icon which opens at this website. An embodiment of the present invention can be implemented to execute when this patient registration icon is clicked by a user. The patient is then instructed to enter the access code which opens their physician's folder. If there are two or more physicians in that office, the patient is instructed to select the tab bearing their physician's name and the registration form opens.

In step 4.3 during registration, the patient is instructed to enter a user name and password. This enables the patient to create a system interaction session. Such a session is maintained after user logout and may be continued at a subsequent login. In this manner, a patient can interrupt the entering of the data of their medical history and re-enter the program at a later time to resume data entry.

In step 4.1.4, the patient medical history interview begins with the Must Answer series of questions after the demographics section is completed. This part of the on-line interview process of an example embodiment enables the patient to tell their physician the primary reason for this appointment (e.g. the reason for the patient's interaction with the on-line medical interview system). The patient is prompted to select a system or location of their body that is causing them some concern. When the patient selects the system of their body where their primary symptom is located, processing control is directed to the section called Chief Complaint where the patient can choose their primary symptom. When the patient chooses their Chief Complaint, they are taken to the section called History of Present Illness where they respond to a series of statements that enable them to describe the origin and development of their present illness or condition. The next screen that opens is a Review of Systems. In this section, the patient tells the physician about any additional symptoms that they are experiencing. Each of these patient queries are described in detail in the examples presented below.

In step 4.1.5, processing control is directed to the Decision Tree where the patient is prompted to provide their Past Medical History, which may or may not be part of the cause of the patient seeing their physician this visit. The past medical history provides the physician with a detailed description of all medical issues in the patient's past. This medical history is provided/entered by the patient her/himself. The Decision Tree reduces the time to complete the interview by sorting out the medical issues that are relevant to the patient.

In step 4.1.6, a progress meter is displayed to inform the patient about how much of the interview is completed. In step 4.1.6.1 and as described in more detail below, the system of various embodiments maintains the statements and choices to which the patient responds while working through the Must Answer series and the Decision Tree.

In step 4.1.7, The Summary contains: a statement of our appreciation for the patient's participation, the patient is informed that they have completed the interview and that their physician has been notified. The patient is invited to review the data that they have entered and to print a copy for their file.

Referring now to FIG. 3, a diagram illustrates an example of a comprehensive, "patient specific" medical history or initial consultation report 305 (also referred to herein as the medical record), which is professionally written in the vocabulary and syntax of physicians as produced by an embodiment of the present invention. The resultant medical record 305 is "chart ready" and capable of being downloaded to the physician's computer prior to the actual evaluation of the patient. This medical record 305 is automatically produced by an embodiment in response to various inputs provided by a patient via a web-based user interface as will be described in more detail below. In this example of a medical record 305, the chief complaint 310 and the history of the present illness 314 are automatically generated by an embodiment in a particular format as defined in a report template 600 (also referred to herein as an output template), an example of which is shown in FIGS. 9A-9C. As will be described in more detail below in a particular example, input provided by a patient/user is mapped to sentence fragments. The sentence fragments are then placed in the medical record 305 at a location defined by the report template 600. Any portion of medical record 305 and any format of medical record 305 can be produced in this manner. A particular example of the automatic production of the comprehensive and "patient specific" medical record 305 is illustrated in FIGS. 3-20 and described in detail below.

Figure 4:
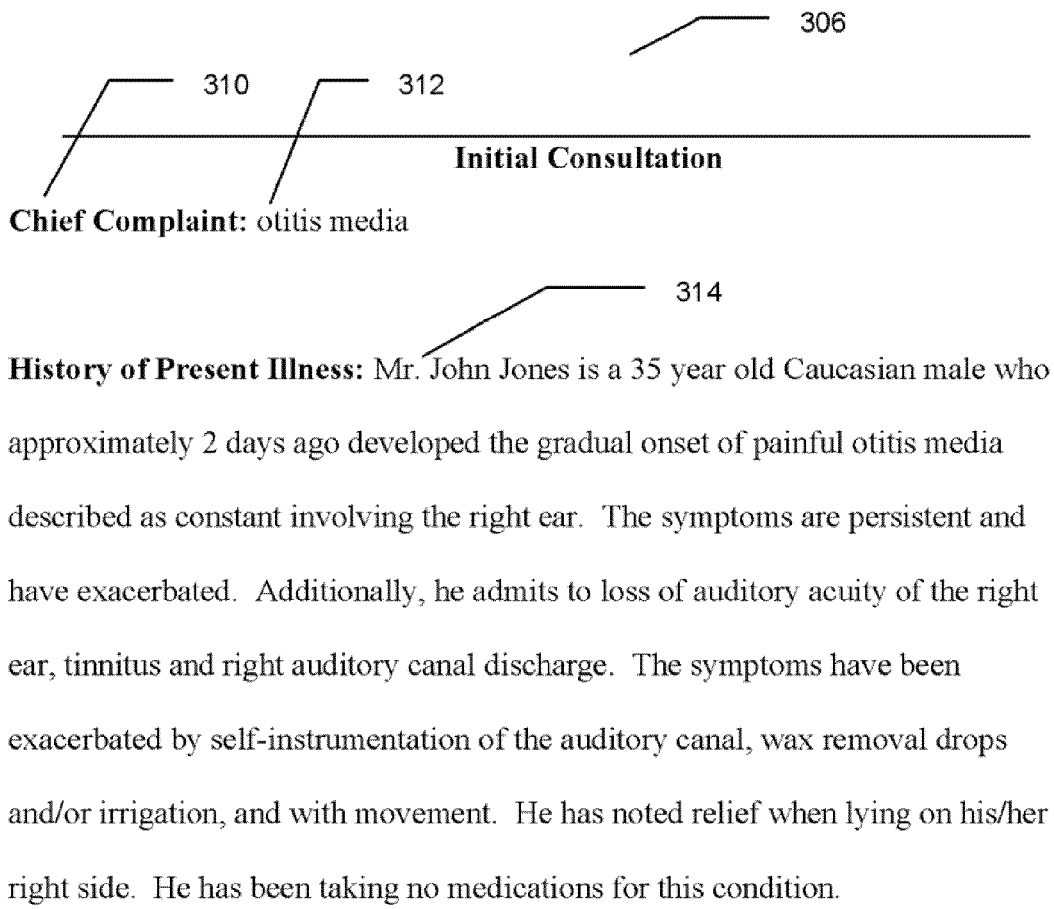
FIG. 4 illustrates an example of the chief complaint portion and the history of the present illness portion of an example medical record.

Referring now to FIG. 4, the chief complaint 310 portion and the history of the present illness 314 portion of medical record 305 from the example of FIG. 3 are reproduced. Based on patient input, an embodiment has inserted the phrase, "otitis media" 312 following the "Chief Complaint" header 310 in medical record 305. The patient has identified this medical condition as his/her chief medical complaint. In the, "History of Present Illness" section, an embodiment has produced grammatically-correct sentences that provide a comprehensive and patient-specific description of the patient based on the patient's responses to various questions prompted by an embodiment.

Figure 6:
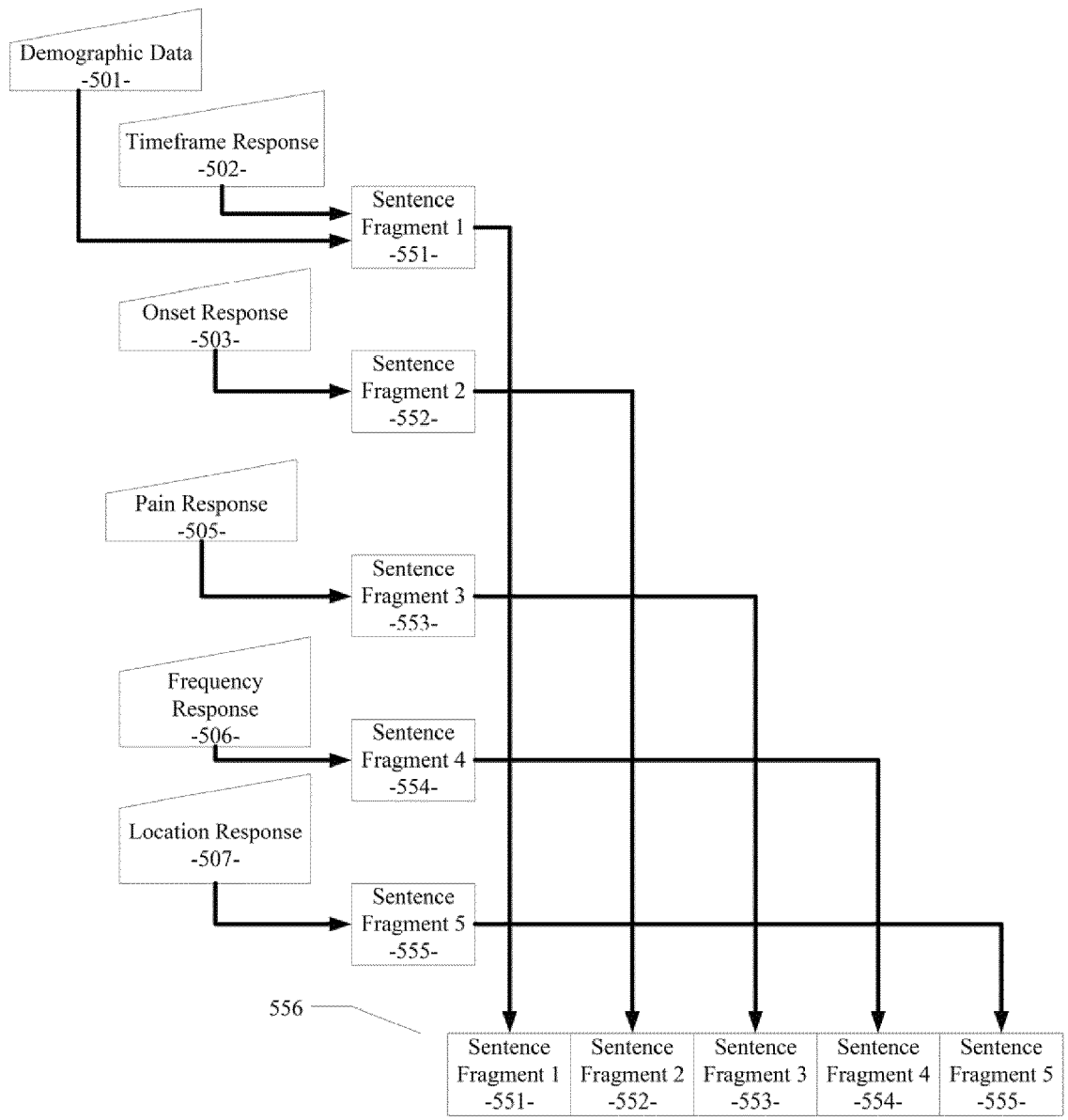
FIG. 6 illustrates a mapping between user inputs and corresponding sentence fragments.

Each of the sentences shown in the history section 314 of report extract 306 can be composed of one or more sentence fragments. Each sentence fragment can be associated with one or more particular inputs provided by the patient via the web-based interface. FIG. 5 illustrates the history section 314 of report extract 306 as partitioned into sentence fragments, each fragment being shown between the "//" symbol. It will be apparent to those of ordinary skill in the art that the sentences of history section 314 could be differently but equivalently partitioned. For example, the first sentence of history section 314 is composed of five sentence fragments, 551-555. First sentence fragment 551 is composed of a set of demographic information (i.e. name, age, race, gender, etc.) that may be automatically extracted from the demographic information input by the patient. The sentence fragment 551 is also composed of timeframe information (i.e. "approximately 2 days ago"). This timeframe information is obtained from the patient in response to a question presented by a particular embodiment. FIG. 6 illustrates the mapping between the patient responses and the corresponding sentence fragments of the first sentence 556 of the example of a particular embodiment.

Referring now to FIG. 6, particular inputs 501-507 provided by a patient can be mapped to particular sentence fragments 551-555 and assembled into a complete sentence 556 for insertion into history section 314 of medical record 305. FIGS. 6-7 illustrate such a mapping for the first sentence of the particular example shown in history section 314 of FIGS. 4-5. Referring again to FIG. 6, demographic information 501 and a timeframe response 502 provided by the patient via the web-based interface is used to automatically create sentence fragment 551. This sentence fragment 551 is detailed in FIG. 7.

Although demographic information 501 can be captured and extracted using conventional techniques, patient responses 502-507 are patient-specific responses to particular medical questions presented by a particular embodiment. The presentation of these medical questions and the processing of the patient responses is detailed next.

Referring now to FIGS. 8A and 8B, a sample spreadsheet illustrates an example of an input template in one embodiment. In a column 410 of the input template, one of the medical questions presented by a particular embodiment is shown. In this case, the patient is prompted to select a medical symptom that best applies to the patient. In this example, the patient is given a set of nine response options (as defined in column 414 in FIG. 8A), which are provided as radio buttons on the web-based interface as defined in column 412 in FIG. 8A. Each of the nine response options are listed in column 416. The sentence or sentence fragment that corresponds to each response option is listed in column 420. Because a response option can be mapped to more than one sentence or sentence fragment, a value in column 418 specifies the quantity of sentences or sentence fragments that correspond to each response option. Thus, for the example shown in FIG. 8A, if a patient selected the first response option (i.e. "loss of hearing") from column 416, the corresponding sentence fragment, "loss of auditory acuity" from column 420 will be automatically inserted into the patient's medical record 305. In this manner, patient responses can be mapped to a corresponding sentence(s) or sentence fragments) that is professionally written in the vocabulary and syntax of physicians. The sentence identifier (ID) provided in column 422 for each response option as shown in FIG. 8A is used to uniquely identify the specific location in the medical record 305 where the mapped sentence(s) or sentence fragment(s) should be automatically placed. Column 424 defines one or more reports or portions of the patient's medical record where the sentence(s) or sentence fragment(s) should be automatically placed. Column 426 can be used to specify a link to which the input engine of a particular embodiment transitions when the corresponding response option is selected by the patient. For example, the link target defined in column 426 can specify a set of follow-on questions that relate to the corresponding response option selected by the patient. In the particular embodiment shown in FIG. 8A, the link in column 426 specifies a particular spreadsheet file to open to produce the set of follow-on questions that relate to the corresponding response option previously selected by the patient. It will be apparent to those of ordinary skill in the art that the link specified in column could also be a hyperlink, a file name, dynamic link library component, an IP address or other type of link to a related software component.

In the particular example provided herein, the patient has selected a response option corresponding to row 428 in FIG. 8B. In this case, the patient has identified an "ear infection" as his primary symptom in response to the question presented from column 410. In response to this selection, the functionality provided by one embodiment retrieves the corresponding sentence fragment, "otitis media" from column 420. The embodiment also retrieves: 1) the sentence ID, "7829" from column 422; 2) the report location, "Report: Chief Complaint:" from column 424 (also denoted herein as the document identifier); and 3) the link information, "\History of Present Illness\Ears System\S_Ears_Otitis Media.xls" from column 426 (the link information identifying a next input prompt). This information is used as described below to insert the sentence fragment "otitis media" from column 420 into the medical record 305 at a location defined by the sentence ID from column 422 and the report location from column 424.

Referring now to FIG. 9A, an example of an extract of an output template of a particular embodiment is shown. In the example embodiment, the structure of a particular output document, in this case an Initial Consultation Report, is defined by the template 600. As shown, the particular document 600 is partitioned into sections that would be expected or mandated by a subscriber, MHP, insurance company, or other healthcare professional or related organization. Within each section, one or more sentence ID's can be listed to provide an anchor point at which a corresponding sentence fragment can be inserted into the output document.

In the particular example described above, a patient had provided a response indicating a symptom corresponding to an ear infection. This response was mapped to the sentence ID, "7829" from column 422 and the report location, "Report: Chief Complaint:" from column 424 shown in FIG. 8B. As shown in FIG. 9A, the report location, "Chief Complaint:" 310 that corresponds to the patient response can be found. Further, the particular location within the specified section of the output document can be found using the sentence ID. In this particular example, the sentence ID, "7829" is located in the "Chief Complaint:" section of output document 600 at location 610. At this specific location of the output document 600, the sentence fragment "otitis media" from column 420 can be inserted. All other sentence ID's and sentence fragments corresponding to responses not selected by the patient can be automatically deleted. As a result, the sentence fragment 312 shown in FIGS. 4-5 can be automatically generated based on an input selected by a patient. In a similar manner, input templates can be used to present patient-specific questions to the patient and to map the particular patient responses to sentence fragments, sentence fragment ID's, and report locations in an output template where the sentence fragments can be inserted.

Referring again to FIGS. 6-7, the first sentence 551 of the example medical record 305 can be automatically generated in a similar manner as described above. Sentence fragment 551 of the particular example is composed of demographic data 501 and a timeframe response 502 provided by the patient/user. Referring to FIGS. 10A-10C and FIG. 11A, a input templates for this example sentence fragment 551 are shown. Referring to FIG. 11A, the patient has previously identified an "ear infection" as his/her chief complaint. Using the link associated with this response as shown in FIG. 8B at column 426, row 428 as described above, the input template shown in FIG. 11A can be obtained and used to present questions to the patient that are related to the patient's specifically identified medical complaint. In this example, the patient is presented with the instructions and the statement/question provided in columns 430 and 431 as shown in FIG. 11A. The patient is thereby prompted to enter the timeframe response 502 as needed for part of sentence fragment 551. In this particular example, the patient selects a response corresponding to a timeframe of, "1-24 hours ago" as shown in column 436 of FIG. 11A. As a result of this selection, the sentence fragment from column 440 of FIG. 11A is retrieved and inserted into the medical record 305 in the "History of Present Illness" section as identified by the information in column 444 of FIG. 11A. Further, the sentence fragment from column 440 of FIG. 11A is retrieved and inserted into the medical record 305 at the location, "8069" as identified by the sentence ID information in column 442 of FIG. 11A.

Referring now to FIG. 9A, the output template 600 is shown. In response to the patient's selection of a timeframe response 502 as described above, the "History of Present Illness" section of output template 600 as identified by the information in column 444 of FIG. 11A is located. Further, the location of the output template 600 identified by the sentence ID, "8069" as identified by the information in column 442 of FIG. 11A is found. This location is identified as location 612 in FIG. 9A. At this location 612, the sentence fragment from column 440 of FIG. 11A is inserted into the medical record 305.

The tags r1, r1a, r1b, r8, and r15/r15a of the sentence fragment from column 440 of FIG. 11A can be replaced with the demographic data 501 obtained from the patient/user at registration time. FIGS. 10A-10C illustrate a few of the input templates for the demographic data 501 of a particular embodiment. Note that the patient-entered first, middle, and last name correspond to tags r1, r1a, and r1b as shown in FIG. 10A at column 462. Similarly, the patient's race corresponds to r8 as shown in FIG. 10C at column 462. Also, the patient's gender corresponds to r15 as shown in FIG. 10C at column 462. In each of these cases, the demographic data provided by the patient can be inserted into the medical record 305 at the location identified in the input templates shown in FIG. 11A and described above.

As a result of the processing described above, the sentence fragment 551 can be inserted into the medical record 305 as part of sentence 556 shown in FIGS. 6 and 7. The generation and insertion of this sentence fragment 551 occurs in response to the patient's entry of the timeframe response 502 along with previous entry of demographic data 501. Next, the patient is prompted to enter the onset response 503. The presentation of the statements/questions related to the onset of the medical condition in this example occurs because a link in column 446 of the previously selected patient response triggers the next automatically presented question or set of questions. In this case, the input template shown in FIG. 11B at row 447 is triggered as a result of the patient's previous response.

Referring now to FIG. 11B, the patient has previously identified "1-24 hours ago" as the timeframe of the medical complaint. Using the link associated with this response as shown in FIG. 11A at column 446, row 445 as described above, the input template shown in FIG. 11B at row 447 can be obtained and used to present questions to the patient that are related to the patient's identified medical complaint. In this example, the patient is presented with the instructions and the statement/question provided in columns 430 and 431 at row 447 as shown in FIG. 11B. The patient is thereby prompted to enter the onset response 503 as needed for sentence fragment 552. In this particular example, the patient selects a response corresponding to a gradual onset as shown in column 436 at row 447 of FIG. 11B. As a result of this selection, the sentence fragment 552, "the gradual onset or" from column 440 at row 447 of FIG. 11B is retrieved and inserted into the medical record 305 in the "History of Present Illness" section as identified by the information in column 444 of FIG. 11B. Further, the sentence fragment 552 from column 440 at row 447 of FIG. 11B is retrieved and inserted into the medical record 305 at the location, "8074" as identified by the information in column 442 at row 447 of FIG. 11B. The insertion of sentence fragment 552 occurs at the location, "8074" as identified in the corresponding location 614 of the output template 600 shown in FIG. 9A. Other responses of output template 600 not corresponding to the patient's response can be deleted.

As a result of the processing described above, the sentence fragment 552 can be inserted into the medical record 305 as part of sentence 556 shown in FIGS. 6 and 7. The generation and insertion of this sentence fragment 552 occurs in response to the patient's entry of the onset response 503 as described above. Next, the patient is prompted to enter the pain response 505. The presentation of the statements/questions related to the pain level of the medical condition in this example occurs because a link in column 446 of the previously selected patient response triggers the next automatically presented question or set of questions. In this case, the input template shown in FIG. 11B at row 448 is triggered as a result of the patient's previous response.

Referring now to FIG. 11B, the patient has previously identified the development of the medical condition as "gradually" in reference to the onset of the medical complaint. Using the link associated with this response as shown in FIG. 11B at column 446, row 447 as described above, the input template shown in FIG. 11B at row 448 can be obtained and used to present questions to the patient that are related to the patient's identified medical complaint. In this example, the patient is presented with the instructions and the statement/question provided in columns 430 and 431 at row 448 as shown in FIG. 11B. The patient is thereby prompted to enter the pain response 505 as needed for sentence fragment 553. In this particular example, the patient selects a response corresponding to "painful" as shown in column 436 at row 448 of FIG. 11B. As a result of this selection, the sentence fragment 553 from column 440 at row 448 of FIG. 11B is retrieved and inserted into the medical record 305 in the "History of Present Illness" section as identified by the information in column 444 of FIG. 11B. Further, the sentence fragment 553 from column 440 at row 448 of FIG. 11B is retrieved and inserted into the medical record 305 at the location, "8076.66" as identified by the information in column 442 at row 448 of FIG. 11B. The insertion of sentence fragment 553 occurs at the location, "8076.66" as identified in the corresponding location 616 of the output template 600 shown in FIG. 9A. Other responses of output template 600 not corresponding to the patient's response can be deleted.

As a result of the processing described above, the sentence fragment 553 can be inserted into the medical record 305 as part of sentence 556 shown in FIGS. 6 and 7. The generation and insertion of this sentence fragment 553 occurs in response to the patient's entry of the pain response 505 as described above. Next, the patient is prompted to enter the frequency response 506. The presentation of the statements/questions related to the frequency of the medical condition in this example occurs because a link in column 446 of the previously selected patient response triggers the next automatically presented question or set of questions. In this case, the input template shown in FIG. 11C at row 449 is triggered as a result of the patient's previous response.

Referring now to FIG. 11C, the patient has previously identified the development of the medical condition as "painful" in reference to the pain level of the medical complaint. Using the link associated with this response as shown in FIG. 11B at column 446, row 448 as described above, the input template shown in FIG. 11C at row 449 can be obtained and used to present questions to the patient that are related to the patient's identified medical complaint. In this example, the patient is presented with the instructions and the statement/question provided in columns 430 and 431 at row 449 as shown in FIG. 11C. The patient is thereby prompted to enter the frequency response 506 as needed for sentence fragment 554. In this particular example, the patient selects a response corresponding to "constant" as shown in column 436 at row 449 of FIG. 11C. As a result of this selection, the sentence fragment 554 from column 440 at row 449 of FIG. 11C is retrieved and inserted into the medical record 305 in the "History of Present Illness" section as identified by the information in column 444 of FIG. 11C. Further, the sentence fragment 554 from column 440 at row 449 of FIG. 11C is retrieved and inserted into the medical record 305 at the location, "8076.68" as identified by the information in column 442 at row 449 of FIG. 11C. The insertion of sentence fragment 554 occurs at the location, "8076.68" as identified in the corresponding location 710 of the output template 600 shown in FIG. 9B. Other responses of output template 600 not corresponding to the patient's response can be deleted.

As a result of the processing described above, the sentence fragment 554 can be inserted into the medical record 305 as part of sentence 556 shown in FIGS. 6 and 7. The generation and insertion of this sentence fragment 554 occurs in response to the patient's entry of the frequency response 506 as described above. Next, the patient is prompted to enter the location response 507. The presentation of the statements/questions related to the location of the medical condition in this example occurs because a link in column 446 of the previously selected patient response triggers the next automatically presented question or set of questions. In this case, the input template shown in FIG. 11C at row 451 is triggered as a result of the patient's previous response.

Referring now to FIG. 11C, the patient has previously identified the development of the medical condition as "constant" in reference to the frequency level of the medical complaint. Using the link associated with this response as shown in FIG. 11C at column 446, row 449 as described above, the input template shown in FIG. 11C at row 451 can be obtained and used to present questions to the patient that are related to the patient's identified medical complaint. In this example, the patient is presented with the instructions and the statement/question provided in columns 430 and 431 at row 451 as shown in FIG. 11C. The patient is thereby prompted to enter the location response 507 as needed for sentence fragment 555. In this particular example, the patient selects a response corresponding to "my right ear" as shown in column 436 at row 451 of FIG. 11C. As a result of this selection, the sentence fragment 555 from column 440 at row 451 of FIG. 11C is retrieved and inserted into the medical record 305 in the "History of Present Illness" section as identified by the information in column 444 of FIG. 11C. Further, the sentence fragment 555 from column 440 at row 451 of FIG. 11C is retrieved and inserted into the medical record 305 at the location, "10016" as identified by the information in column 442 at row 451 of FIG. 11C. The insertion of sentence fragment 555 occurs at the location, "10016" as identified in the corresponding location 712 of the output template 600 shown in FIG. 9B. Other responses of output template 600 not corresponding to the patient's response can be deleted.

As a result of the processing described above, the sentence fragment 555 can be inserted into the medical record 305 as part of sentence 556 shown in FIGS. 6 and 7. The generation and insertion of this sentence fragment 555 occurs in response to the patient's entry of the location response 507 as described above. This completes the compilation of the sentence fragments corresponding to the first sentence 556 of the example medical record 305.

Figure 12:
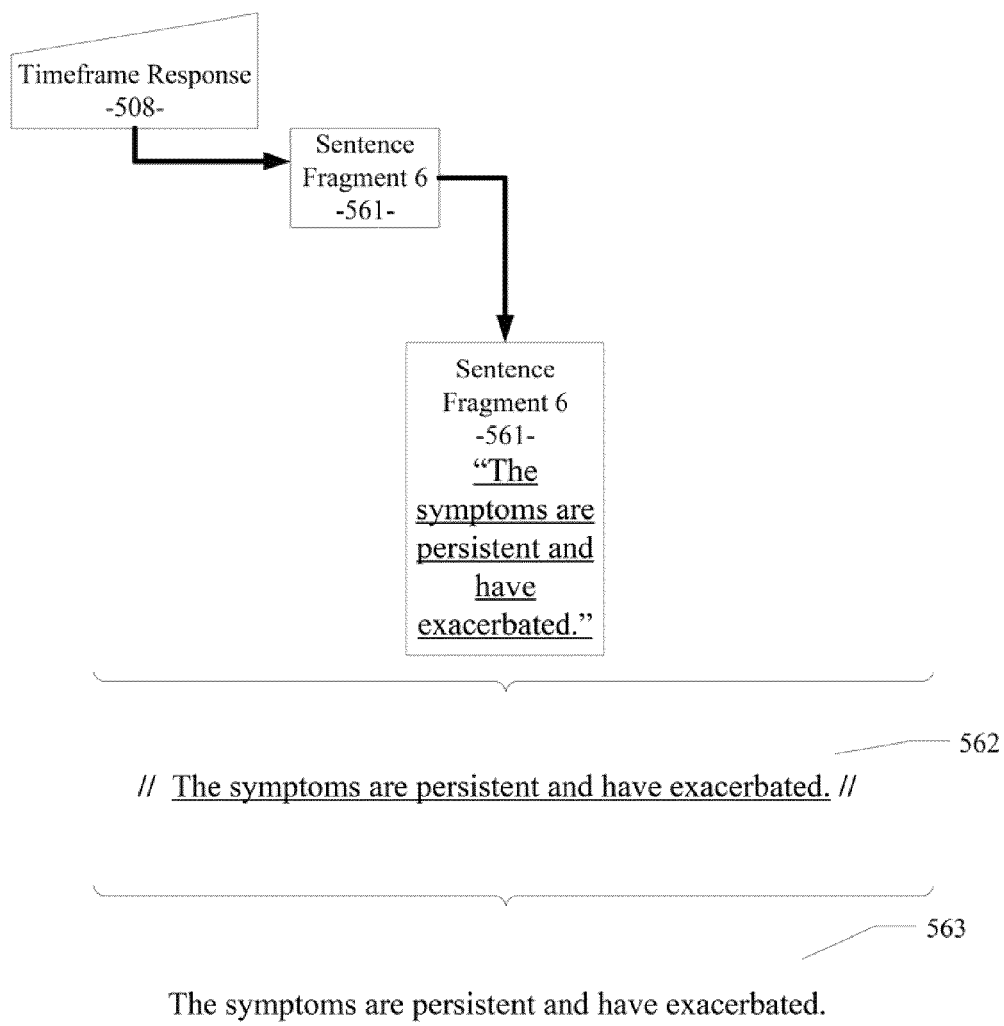
FIG. 12 illustrates a mapping between user input and a corresponding sentence fragment along with a detail of the sentence fragment for a particular example.

Referring now to FIG. 12, the second sentence 563 of the example medical record 305 is illustrated in relation to the patient input that maps to the automatically generated sentence. In this case, the patient is prompted to enter the timeframe response 508. The presentation of the statements/questions related to the timeframe of the medical condition in this example occurs because a link in column 446 of the previously selected patient response triggers the next automatically presented question or set of questions. In this case, the input template shown in FIG. 11C at row 453 is triggered as a result of the patient's previous response.

Referring now to FIG. 11C, the patient has previously identified the development of the medical condition as involving, "my right ear" in reference to the location of the medical complaint. Using the link associated with this response as shown in FIG. 11C at column 446, row 451 as described above, the input template shown in FIG. 11C at row 453 and 455 can be obtained and used to present questions to the patient that are related to the patient's identified medical complaint. In this example, the patient is presented with the instructions and the statement/question provided in columns 430 and 431 at row 455 as shown in FIG. 11C. The patient is thereby prompted to enter the timeframe response 508 as needed for sentence fragment 561. In this particular example, the patient selects a response corresponding to "my persistent symptoms have worsened" as shown in column 436 at row 453 of FIG. 11C. As a result of this selection, the sentence fragment 561 from column 440 at row 453 of FIG. 11C is retrieved and inserted into the medical record 305 in the "History of Present Illness" section as identified by the information in column 444 of FIG. 11C. Further, the sentence fragment 561 from column 440 at row 453 of FIG. 11C is retrieved and inserted into the medical record 305 at the location, "8126.1" as identified by the information in column 442 at row 453 of FIG. 11C. The insertion of sentence fragment 561 occurs at the location, "8126.1" as identified in the corresponding location 714 of the output template 600 shown in FIG. 9B. Other responses of output template 600 not corresponding to the patient's response can be deleted.

As a result of the processing described above, the sentence fragment 561 can be inserted into the medical record 305 as shown in FIG. 12. The generation and insertion of this sentence fragment 561 occurs in response to the patient's entry of the timeframe response 508 as described above. This completes the compilation of the sentence fragments corresponding to the second sentence 561 of the example medical record 305.

Figure 13:
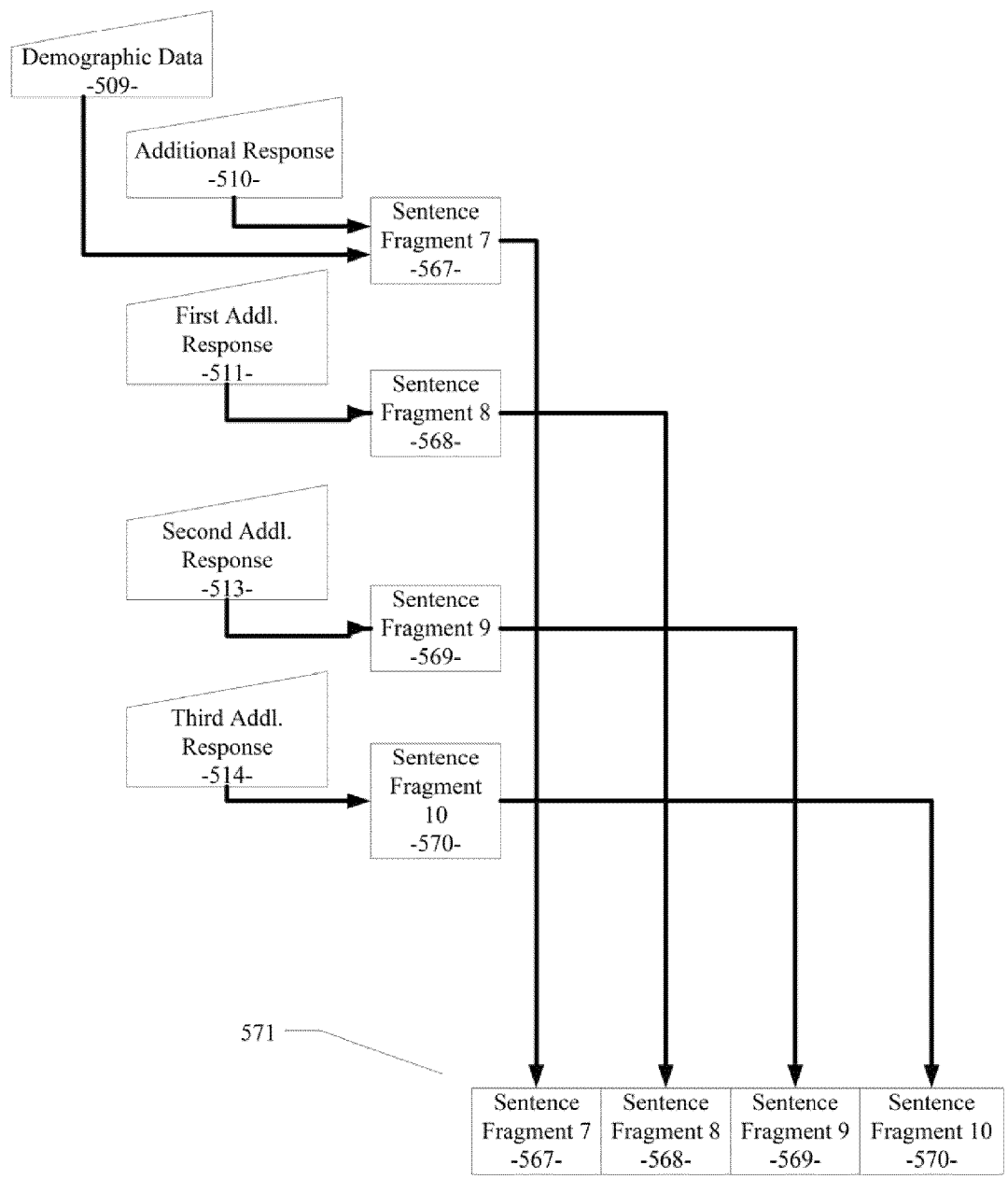
FIG. 13 illustrates a mapping between user inputs and corresponding sentence fragments.

Referring now to FIG. 13, the third sentence 571 of the example medical record 305 is illustrated in relation to the patient input that maps to the automatically generated sentence. In this case, the patient is initially prompted to enter any additional medical conditions as an additional response 510. The presentation of the statements/questions related to any additional medical conditions in this example occurs because a link in column 446 of the previously selected patient response triggers the next automatically presented question or set of questions. In this case, the input template shown in FIG. 11D at row 457 is triggered as a result of the patient's previous response.

Referring now to FIG. 11D, the patient has previously identified the development of the medical condition as, "my persistent symptoms have worsened" in reference to the timeframe response 508 of the medical complaint. Using the link associated with this response as shown in FIG. 11C at column 446, row 453 as described above, the input template shown in FIG. 11D at row 457 can be obtained and used to present questions to the patient that are related to the patient's identified medical complaint. In this example, the patient is presented with the instructions and the statement/question provided in columns 430 and 431 at row 457 as shown in FIG. 11D. The patient is thereby prompted to enter the additional response 510 as needed for sentence fragment 567. In this particular example, the patient selects a response corresponding to "TRUE" as shown in column 436 at row 457 of FIG. 11D. As a result of this selection, the sentence fragment 567 from column 440 at row 457 of FIG. 11D is retrieved and inserted into the medical record 305 in the "History of Present Illness" section as identified by the information in column 444 of FIG. 11D. Further, the sentence fragment 567 from column 440 at row 457 of FIG. 11D is retrieved and inserted into the medical record 305 at the location, "8082" as identified by the information in column 442 at row 457 of FIG. 11D. The insertion of sentence fragment 567 occurs at the location, "8082" as identified in the corresponding location 716 of the output template 600 shown in FIG. 9B. Other responses of output template 600 not corresponding to the patient's response can be deleted.

As a result of the processing described above, the sentence fragment 567 can be inserted into the medical record 305 as shown in FIG. 13. The generation and insertion of this sentence fragment 567 occurs in response to the patient's entry of the additional response 510 as described above. Next, the patient is prompted to enter the first additional response 511. The presentation of the statements/questions related to the first additional symptom of the medical condition in this example occurs because a link in column 446 of the previously selected patient response triggers the next automatically presented question or set of questions. In this case, the input template shown in FIG. 14 at row 461 is triggered as a result of the patient's previous response.

Referring now to FIG. 14, the patient has previously identified the development of the medical, condition as having additional symptoms. Using the link associated with this response as shown in FIG. 11D at column 446, row 457 as described above, the input template shown in FIG. 14 at row 461 can be obtained and used to present questions to the patient that are related to the patient's identified medical complaint. In this example, the patient is presented with the instructions and the statement/question provided in columns 430 and 431 at row 461 as shown in FIG. 14. The patient is thereby prompted to enter the first additional response 511 as needed for sentence fragment 568. In this particular example, the patient selects a response corresponding to "loss of hearing in my right ear" as shown in column 436 at row 461 of FIG. 14. As a result of this selection, the sentence fragment 568 from column 440 at row 461 of FIG. 14 is retrieved and inserted into the medical record 305 in the "History of Present Illness" section as identified by the information in column 444 of FIG. 14. Further, the sentence fragment 568 from column 440 at row 461 of FIG. 14 is retrieved and inserted into the medical record 305 at the location, "8428" as identified by the information in column 442 at row 461 of FIG. 14. The insertion of sentence fragment 568 occurs at the location, "8428" as identified in the corresponding location 718 of the output template 600 shown in FIG. 9B. Other responses of output template 600 not corresponding to the patient's response can be deleted.

Figure 15:
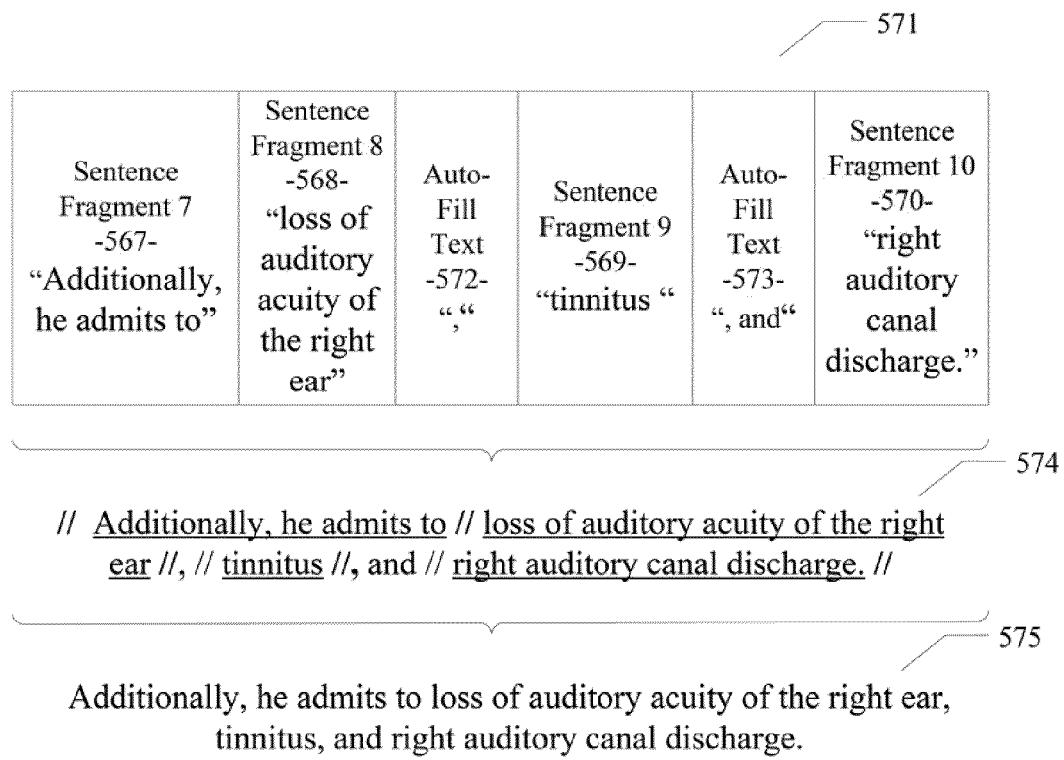
FIG. 15 is a detail of the sentence fragments for a particular example.

As a result of the processing described above, the sentence fragment 568 can be inserted into the medical record 305 as part of sentence 571 shown in FIGS. 13 and 15. The generation and insertion of this sentence fragment 568 occurs in response to the patient's entry of the first additional response 511 as described above. Next, the patient is prompted to enter the second additional response 513.

Referring now to FIG. 14, the patient is prompted to enter the second additional response 513 as needed for sentence fragment 569. In this particular example, the patient selects a response corresponding to "recurrent ringing in the ears" as shown in column 436 at row 463 of FIG. 14. As a result of this selection, the sentence fragment 569 from column 440 at row 463 of FIG. 14 is retrieved and inserted into the medical record 305 in the "History of Present Illness" section as identified by the information in column 444 of FIG. 14. Further, the sentence fragment 569 from column 440 at row 463 of FIG. 14 is retrieved and inserted into the medical record 305 at the location, "8430" as identified by the information in column 442 at row 463 of FIG. 14. The insertion of sentence fragment 569 occurs at the location, "8430" as identified in the corresponding location 720 of the output template 600 shown in FIG. 9B. Other responses of output template 600 not corresponding to the patient's response can be deleted.

As a result of the processing described above, the sentence fragment 569 can be inserted into the medical record 305 as part of sentence 571 shown in FIGS. 13 and 15. The generation and insertion of this sentence fragment 569 occurs in response to the patient's entry of the second additional response 513 as described above. Next, the patient is prompted to enter the third additional response 514.

Referring now to FIG. 14, the patient is prompted to enter the third additional response 514 as needed for sentence fragment 570. In this particular example, the patient selects a response corresponding to "discharge from my right ear" as shown in column 436 at row 465 of FIG. 14. As a result of this selection, the sentence fragment 570 from column 440 at row 465 of FIG. 14 is retrieved and inserted into the medical record 305 in the "History of Present Illness" section as identified by the information in column 444 of FIG. 14. Further, the sentence fragment 570 from column 440 at row 465 of FIG. 14 is retrieved and inserted into the medical record 305 at the location, "8432" as identified by the information in column 442 at row 465 of FIG. 14. The insertion of sentence fragment 570 occurs at the location, "8432" as identified in the corresponding location 722 of the output template 600 shown in FIG. 9B. Other responses of output template 600 not corresponding to the patient's response can be deleted.

Because the first, second, and third additional responses 511, 513, and 514 are presented to the patient/user as a list, the system of a particular embodiment can automatically insert auto-fill text 572 and 573 into sentence 571 as shown in FIG. 15. In this case, a ",", after sentence fragment 568 and a ", and" can be inserted after sentence fragment 569. This completes the compilation of the sentence fragments corresponding to the third sentence 571 of the example medical record 305.

Figure 16:
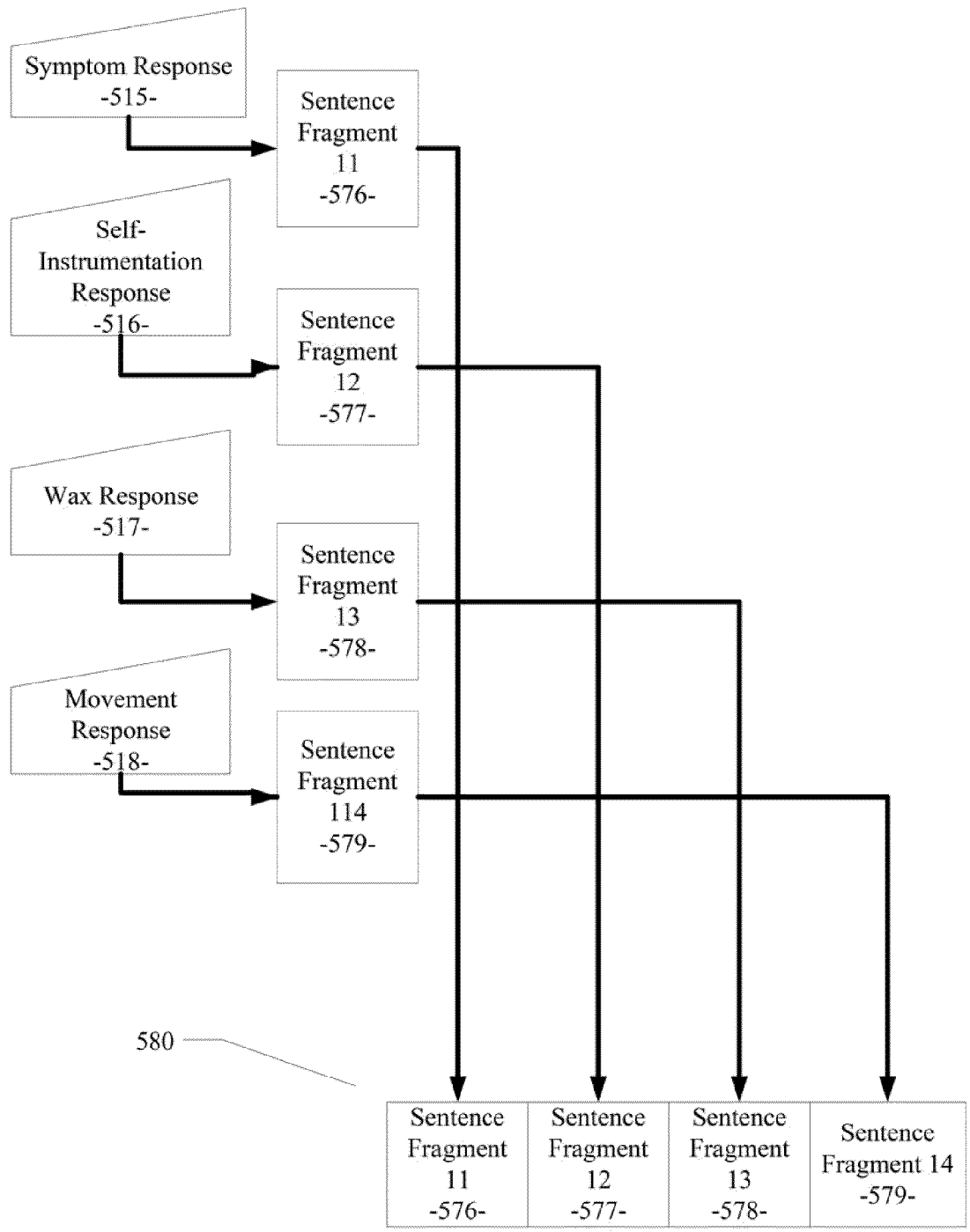
FIG. 16 illustrates a mapping between user inputs and corresponding sentence fragments.

Referring now to FIG. 16, the fourth sentence 580 of the example medical record 305 is illustrated in relation to the patient input that maps to the automatically generated sentence. In this case, the patient is initially prompted to enter any exacerbating medical conditions as symptom response 515. The presentation of the statements/questions related to any exacerbating medical conditions in this example occurs because a link in column 446 of the previously selected patient response triggers the next automatically presented question or set of questions. In this case, the input template shown in FIG. 11E at row 459 is triggered as a result of the patient's previous response.

Referring now to FIG. 11E, using the link associated with the previous response, the input template shown in FIG. 11E at row 459 can be obtained and used to present questions to the patient that are related to the patient's identified medical complaint. In this example, the patient is presented with the instructions and the statement/question provided in columns 430 and 431 at row 459 as shown in FIG. 11E. The patient is thereby prompted to enter the symptom response 515 as needed for sentence fragment 576. In this particular example, the patient selects a response corresponding to "TRUE" as shown in column 436 at row 459 of FIG. 11E. As a result of this selection, the sentence fragment 576 from column 440 at row 459 of FIG. 11E is retrieved and inserted into the medical record 305 in the "History of Present Illness" section as identified by the information in column 444 of FIG. 11E. Further, the sentence fragment 576 from column 440 at row 459 of FIG. 11E is retrieved and inserted into the medical record 305 at the location, "8151" as identified by the information in column 442 at row 459 of FIG. 11E. The insertion of sentence fragment 576 occurs at the location, "8151" as identified in the corresponding location 810 of the output template 600 shown in FIG. 9C. Other responses of output template 600 not corresponding to the patient's response can be deleted.

As a result of the processing described above, the sentence fragment 576 can be inserted into the medical record 305 as shown in FIGS. 16 and 17. Similarly, sentence fragments 577, 578, and 579 can be automatically generated based on the inputs 516, 517, and 518, respectively as described in detail above. Thus, sentence 580 can be inserted into the medical record 305 at the appropriate locations as shown in FIG. 9C.

Figure 18:
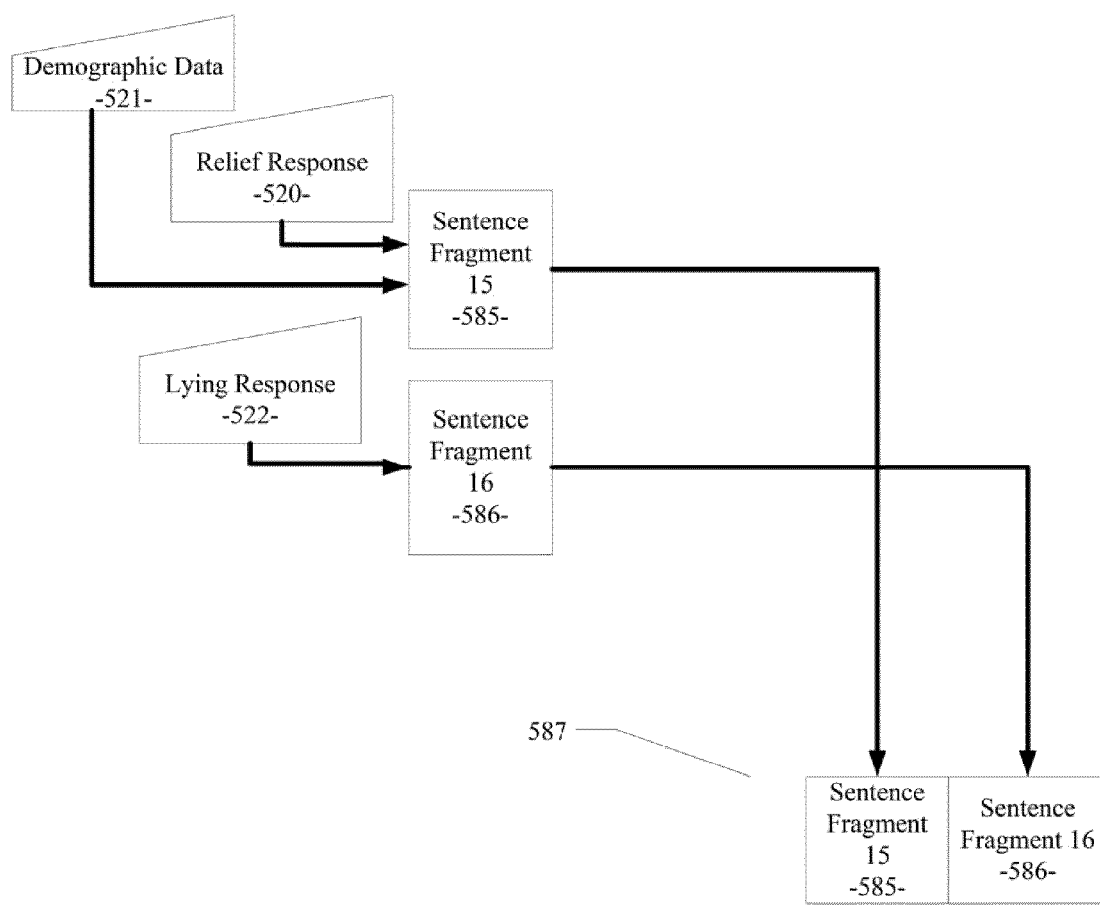
FIG. 18 illustrates a mapping between user inputs and corresponding sentence fragments.
Figure 20:
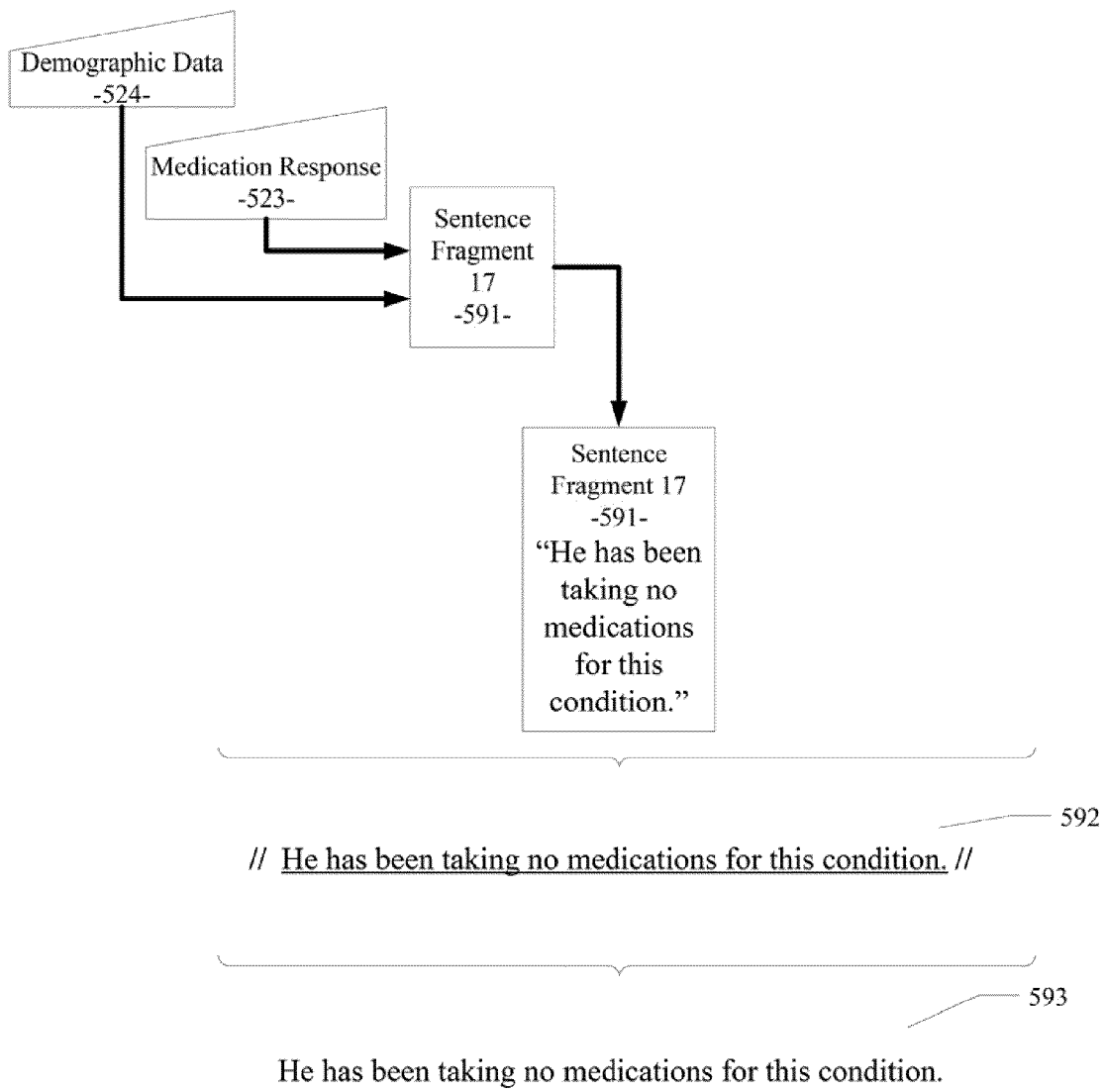
FIG. 20 illustrates a mapping between user input and a corresponding sentence fragment along with a detail of the sentence fragment for a particular example.

In a manner similar to the processes described above, the remaining sentences 589 and 593 illustrated in FIGS. 18-20 can be automatically generated and inserted into the medical report 305 at the appropriate location.

Figure 21:
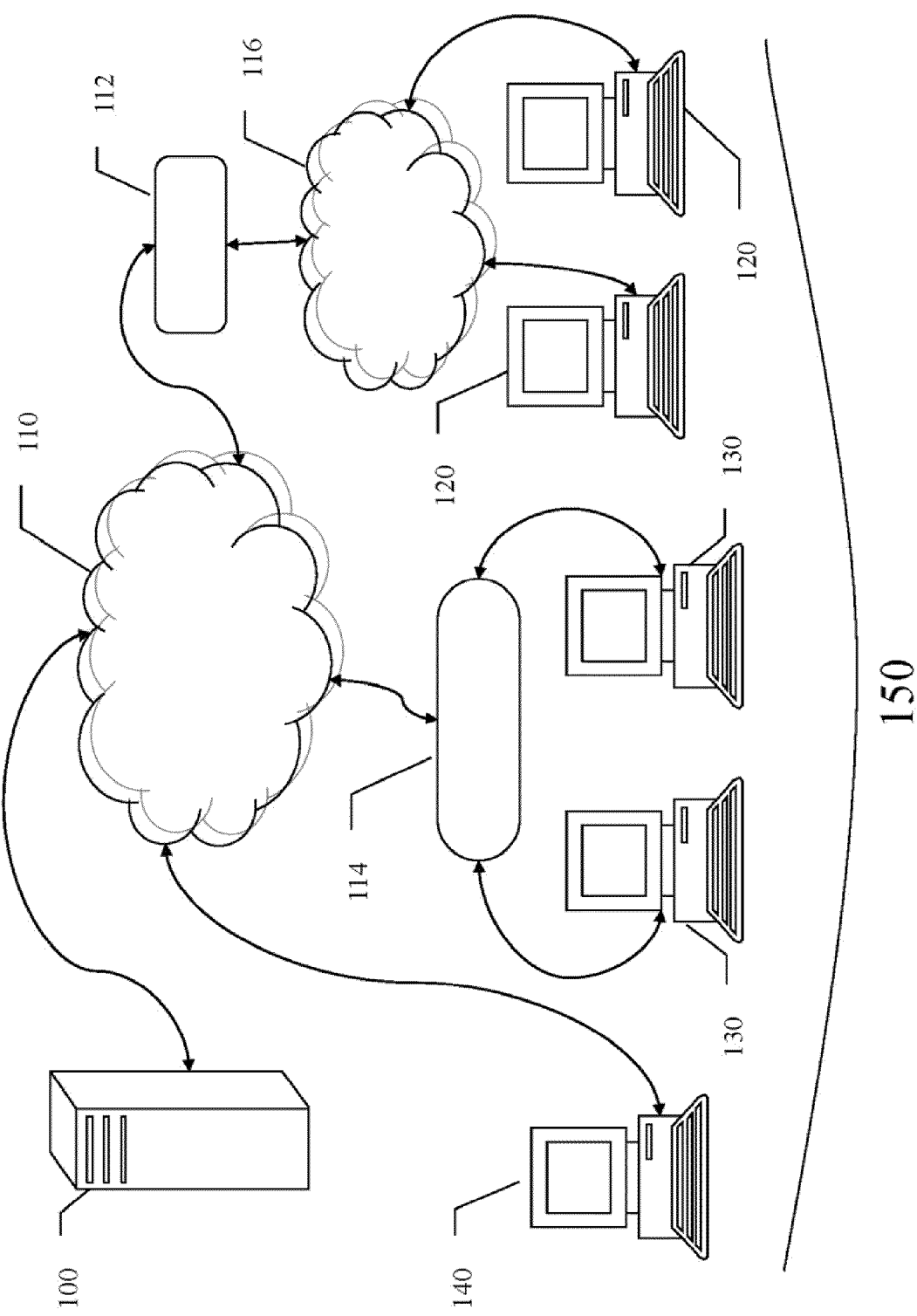
FIGS. 21-23 illustrate an example embodiment of a computing system in accordance with the disclosed subject matter.

Referring now to FIG. 21, a diagram illustrates the network environment in which various embodiments can operate. In this conventional network architecture, a server computer system 100 is coupled to a wide-area network 110. Wide-area network 110 includes the Internet, or other proprietary networks, which are well known to those of ordinary skill in the art. Wide-area network 110 may include conventional network backbones, long-haul telephone lines, Internet service providers, various levels of network routers, and other conventional means for routing data between computers. Using conventional network protocols, server 100 may communicate through wide-area network 110 to a plurality of client computer systems 120, 130, 140 connected through wide-area network 110 in various ways. For example, client 140 is connected directly to wide-area network 110 through direct or dial-up telephone or other network transmission line. Alternatively, clients 130 may be connected through wide-area network 110 using a modem pool 114. A conventional modem pool 114 allows a plurality of client systems to connect with a smaller set of modems in modem pool 114 for connection through wide-area network 110. In another alternative network topology, wide-area network 110 is connected to a gateway computer 112. Gateway computer 112 is used to route data to clients 120 through a local area network (LAN) 116. In this manner, clients 120 can communicate with each other through local area network 116 or with server 100 through gateway 112 and wide-area network 110.

Using one of a variety of network connection means, server computer 100 can communicate with client computers 150 using conventional means. In a particular implementation of this network configuration, a server computer 100 may operate as a web server if the Internet's World-Wide Web (WWW) is used for wide area network 110. Using the HTTP protocol and the HTML coding language across wide-area network 110, web server 100 may communicate across the World-Wide Web with clients 150. In this configuration, clients 150 use a client application program known as a web browser such as the Internet Explorer™ published by Microsoft Corporation of Redmond, Wash., the user interface of America On-Line™, or the web browser or HTML renderer of any other supplier. Using such conventional browsers and the World-Wide Web, clients 150 may access image, graphical, and textual data provided by web server 100 or they may run Web application software. Conventional means exist by which clients 150 may supply information to web server 100 through the World Wide Web 110 and the web server 100 may return processed data to clients 150.

Figure 22:
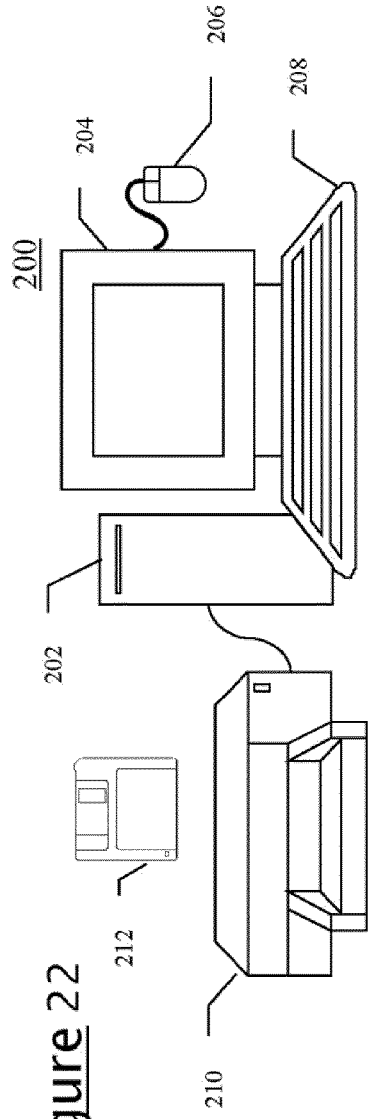
Figure 23:
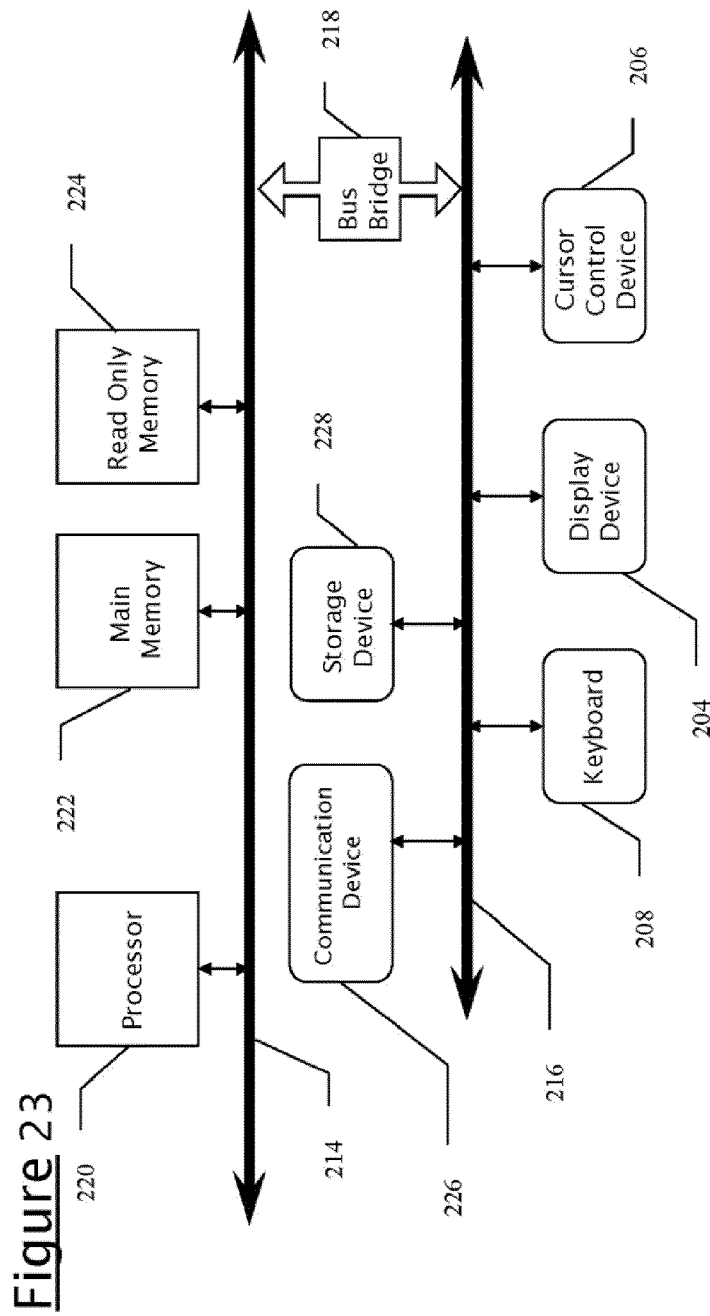

Having briefly described one embodiment of the network environment in which various embodiments may operate, FIGS. 22 and 23 show an example of a computer system 200 illustrating an exemplary host, client, or server computer system, in which the features of an example embodiment may be implemented. Computer system 200 is comprised of a bus or other communications means 214 and 216 for communicating information, and a processing means such as processor 220 coupled with bus 214 for processing information. Computer system 200 further comprises a random access memory (RAM) or other dynamic storage device 222 (commonly referred to as main memory), coupled to bus 214 for storing information and instructions to be executed by processor 220. Main memory 222 also may be used for storing temporary variables or other intermediate information during execution of instructions by processor 220. Computer system 200 also comprises a read only memory (ROM) and/or other static storage device 224 coupled to bus 214 for storing static information and instructions for processor 220.

An optional data storage device 228 such as a magnetic disk or optical disk and its corresponding drive may also be coupled to computer system 200 for storing information and instructions. Computer system 200 can also be coupled via bus 216 to a display device 204, such as a cathode ray tube (CRT) or a liquid crystal display (LCD), for displaying information to a computer user. For example, image, textual, video, or graphical depictions of information may be presented to the user on display device 204. Typically, an alphanumeric input device 208, including alphanumeric and other keys is coupled to bus 216 for communicating information and/or command selections to processor 220. Another type of user input device is cursor control device 206, such as a conventional mouse, trackball, or other type of cursor direction keys for communicating direction information and command selection to processor 220 and for controlling cursor movement on display 204.

Alternatively, the client 280 can be implemented as a network computer or thin client device. Client 280 may also be a laptop or palm-top computing device, such as the Palm Pilot™. Client 280 could also be implemented in a robust cellular telephone, where such devices are currently being used with Internet micro-browsers. Such a network computer or thin client device does not necessarily include all of the devices and features of the above-described exemplary computer system; however, the functionality of an example embodiment or a subset thereof may nevertheless be implemented with such devices.

A communication device 226 is also coupled to bus 216 for accessing remote computers or servers, such as web server 250, or other servers via the Internet, for example. The communication device 226 may include a modem, a network interface card, or other well-known interface devices, such as those used for interfacing with Ethernet, Token-ring, or other types of networks. In any event, in this manner, the computer system 200 may be coupled to a number of servers 250 via a conventional network infrastructure such as the infrastructure illustrated and described above.

The system of an example embodiment includes software, information processing hardware, and various processing steps, which are described above. The features and process steps of example embodiments may be embodied in machine or computer executable instructions. The instructions can be used to cause a general purpose or special purpose processor, which is programmed with the instructions to perform the steps of an example embodiment. Alternatively, the features or steps may be performed by specific hardware components that contain hard-wired logic for performing the steps, or by any combination of programmed computer components and custom hardware components. While embodiments are described with reference to the Internet, the method and apparatus described herein is equally applicable to other network infrastructures or other data communications systems.

Various embodiments are described. In particular, the use of embodiments with various types and formats of data structures may be described. It will be apparent to those of ordinary skill in the art that alternative embodiments of the implementations described herein can be employed and still fall within the scope of the claimed invention. In the detail herein, various embodiments are described as implemented in computer-implemented processing logic denoted sometimes herein as the "Software". As described above, however, the claimed invention is not limited to a purely software implementation.

The software and/or data described herein may further be transmitted or received over a network 280 via a communication device 226 utilizing any one of a number of well-known transfer protocols, for example, the hyper text transfer protocol (HTTP). While the machine-readable medium 212 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any non-transitory medium that is capable of storing, encoding, or carrying a set of instructions for execution by the machine and that cause the machine to perform any one or more of the methodologies of the disclosed subject matter, or that is capable of storing, encoding, or carrying data structures utilized by or associated with such a set of instructions. The term "machine-readable medium" shall accordingly be taken to include, but not be limited to, solid-state memories and optical and magnetic media.

Although the present specification describes components and functions implemented in the embodiments with reference to particular standards and protocols, the disclosed subject matter may be not limited to such standards and protocols. Each of the standards for Internet and other packet switched network transmission (e.g., TCP/IP, UDP/IP, HTML, and HTTP) represent examples of the state of the art. Such standards are periodically superseded by faster or more efficient equivalents having essentially the same functions. Accordingly, replacement standards and protocols having the same functions are considered equivalents.

Figure 24:
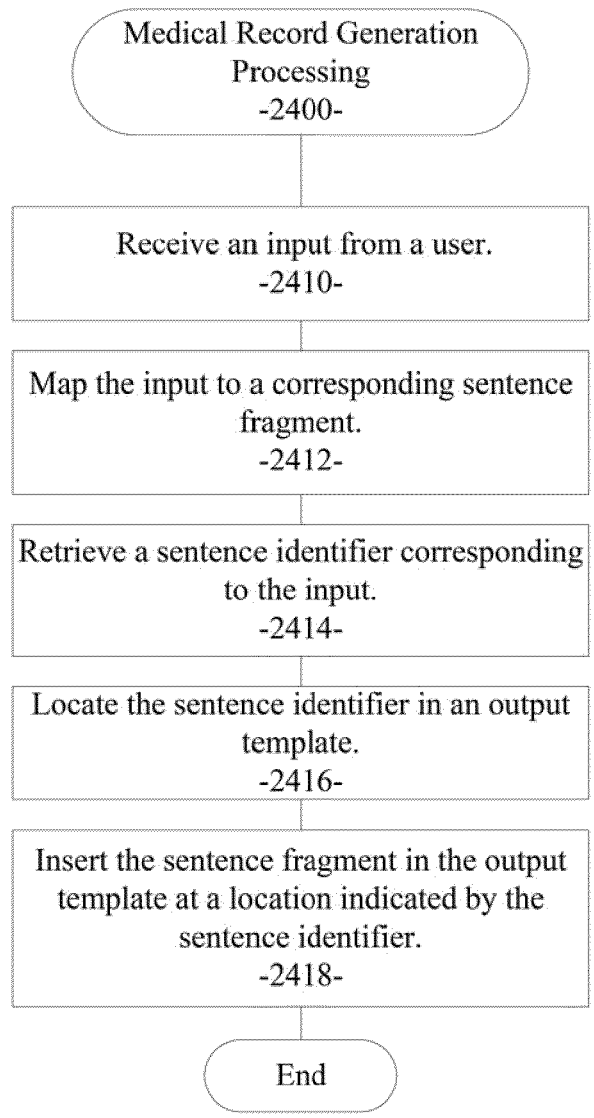
FIG. 24 is a flow diagram illustrating a processing flow in a particular embodiment.

Referring now to FIG. 24, a flow diagram illustrates a processing flow in a particular embodiment. As illustrated, the method in a particular embodiment includes: receiving an input from a user, mapping the input to a corresponding sentence fragment, retrieving a sentence identifier corresponding to the input, locating the sentence identifier in an output template, and inserting the sentence fragment in the output template at a location indicated by the sentence identifier. Details of the method in a particular embodiment are provided above.

Referring now to FIGS. 25 through 33 as described below, a particular example embodiment illustrates a structure, processing flow, and operation of the system and method of a particular embodiment. As illustrated and described herein, the example system and method demonstrate a particular embodiment for automatically generating patient-specific and grammatically correct electronic medical records. In this particular example, the Ruby programming language is used to implement the example embodiment. The Ruby programming language or Ruby is a dynamic, reflective, general-purpose object-oriented programming language that combines syntax inspired by Perl with Smalltalk-like features. In Ruby, bindings are explicitly made available in a Binding object. Invoking the binding method can produce a Binding object for the current local variables. Using the Ruby binding method, the variable bindings available at a particular point in the code can be captured and passed to a different part of the code to be used there. For example, as described in more detail below, the Ruby binding method enables a sentence template to access the data bindings and defined macros that can inject grammatically correct conjugations and gender correct pronouns based on specific patient data and demographics bindings. The Ruby programming language in general is well-known to those of ordinary skill in the art. It will be apparent to those of ordinary skill in the art that other equivalent programming languages, protocols, or paradigms can also be used to implement the various embodiments described herein.

The particular example embodiment described herein is implemented as a web application running on a server computer system 100, which is coupled to a wide-area network 110 (e.g., see FIG. 21). Wide-area network 110 includes the Internet, or other proprietary networks, which are well known to those of ordinary skill in the art. Using conventional network protocols, server 100 may communicate through wide-area network 110 to a plurality of client computer systems 120, 130, and 140 connected through wide-area network 110 in various conventional ways. Client computer systems 120, 130, and 140 can connect and interact with the web application running on a server computer system 100. The web application can provide a plurality of client-facing user interface paradigms with which various types of users, operating client computer systems 120, 130, and 140, can interact with the web application. In a particular type of user interface paradigm, different websites or sites are provided to enable different types of users to interact with the web application. For example, as described in more detail below, a first site is provided for patients to interact with a front end of the web application. A second site is provided for administrative personnel to interact with a back end or back office portion of the web application. In this manner, different types of users can use and/or configure the web application.

Figure 25:
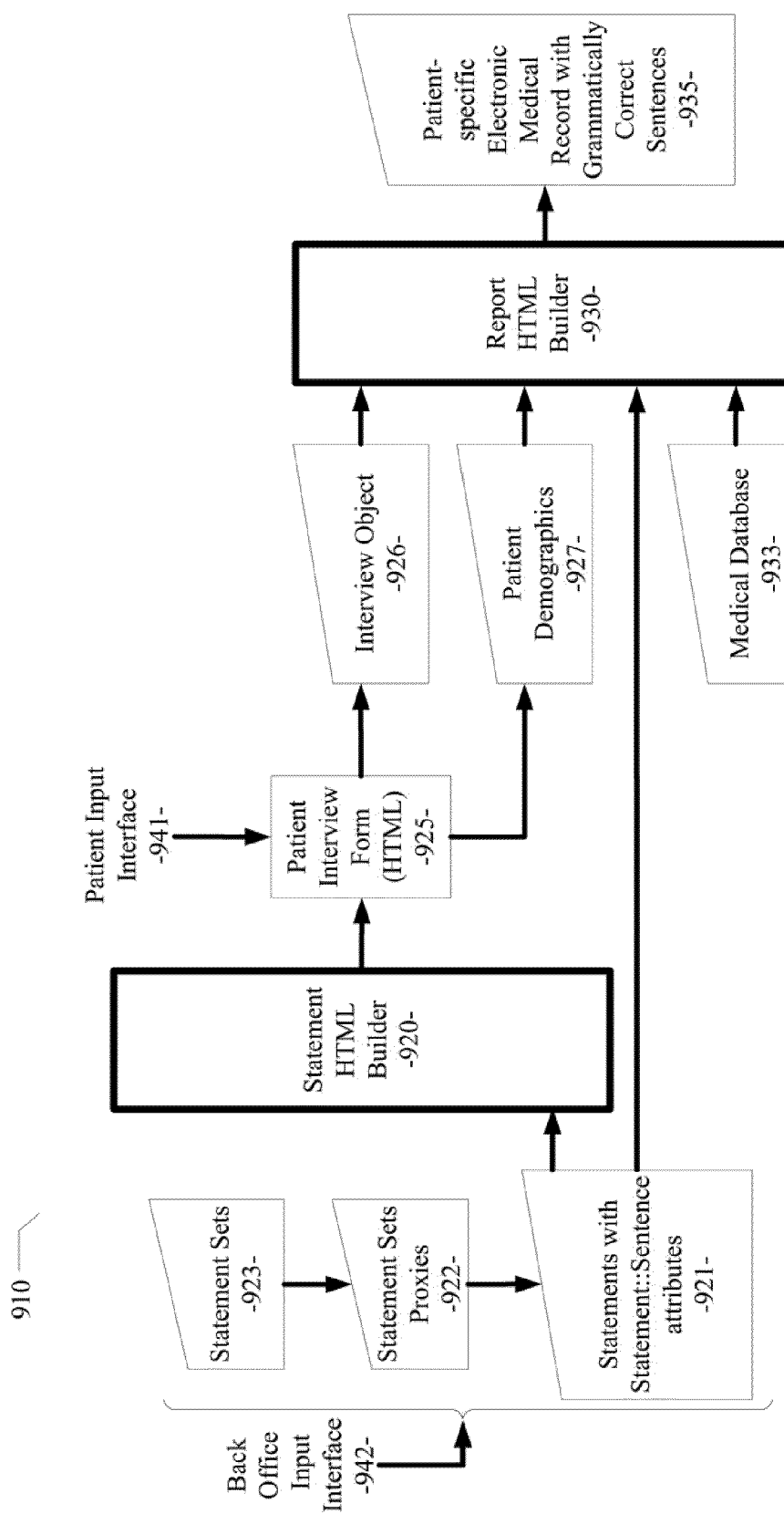
FIG. 25 illustrates an example implementation of a particular system of an example embodiment.

A particular example embodiment described herein is illustrated in FIG. 25. Referring to FIG. 25, a state machine (also called a statement builder, denoted herein as StatementHTMLBuilder 920), running as part of the web application 910 on server 100, processes Statements 921, ordered and grouped by StatementSets 923, which are further ordered and grouped by StatementSetProxies 922. Depending on the type of Statement 921 and its control options, a patient interview form or HTML (Hypertext Markup Language) form 925 is generated to interview a patient and collect specific patient data. The collected patient data is retained in an Interview object 926. Additionally, a set of patient-specific demographic information can be collected from a patient using the same or a different patient interview form. The set of patient-specific demographic information can be retained in a patient demographics objector dataset 927.

Referring still to FIG. 25, a ReportHTMLBuilder state machine 930 (also called a report builder), running as part of the web application 910 on server 100, can then be used to generate patient-specific and grammatically correct sentences 935 using the Statement::sentence attribute of Statements 921 as a template, based on patient data and demographics 927, interview data 926, and statement structures 921. Additionally, the ReportHTMLBuilder state machine 930 can be configured to pull patient-specific, demographic-specific, and/or medical condition-specific data from one or more medical databases 933 for insertion into the patient-specific and grammatically correct sentences 935. The medical databases 933 can be internally-generated datasets and/or $3^{rd}$ party medical databases generated by others. In this manner, an electronic medical record (EMR) 935 with patient-specific and grammatically correct sentences can be automatically generated by the web application 910 of a particular embodiment. The patient-specific and grammatically correct sentences 935 can be deemed grammatically correct provided the Statement object 921 is configured correctly. Specifically, sentences can be deemed grammatically correct provided the template (Statement::sentence attribute of Statements 921) is configured with the appropriate data and the sentence record is positioned correctly within the StatementSet 923. This configuration of Statement object 921, Statement Sets Proxies 922, and Statement Sets 923 can be accomplished using the administrative services provided by the back office site interface 942 as shown in FIG. 25 and described in more detail below.

In the particular example embodiment described herein, the web application 910 provides two user perspectives, Patient and Back Office. As described above, the Patient and Back Office perspectives can be implemented as two different sites with different user interfaces (941 and 942) for accessing the web application 910. The Patient site interface 941 exposes public URLs (Uniform Resource Locators) linked to Patient records for the purpose of conducting a patient interview and for receiving patient input data in a patient interview form 925 via patient site interface 941. The Back Office site interface 942 is typically for host administrative staff use only. The Back Office site is used by host administrative staff to create, configure, and modify Statements 921, StatementSets 923, and other key data objects used by the web application 910 for processing patient input into EMR 935. The Back Office site is also used to provide administrative services for patients. These key data objects implemented and used in the particular example embodiment are described in more detail below.

Statement Object

A statement of statements 921, as used in the particular example embodiment, is the base object for presenting information, instructions, and/or questions to a user/patient during the patient interview process. The patient's answer (StatementResponse) to a question can be retained separately and used with the statement to generate a dictated response as part of the corresponding output EMR 935. The statement object can also be sub-classed to enable business logic, using a base options attribute, for example, to serialize statement options. The statement object options attribute can thus be used to drive the logic of the statement and to serialize a set of operations performed in association with the logic of the statement. In this manner, various statements can be configured, for example, to present instructions and questions to a patient along with a configurable set of response options. Statements can also be configured, using a statement object, to gather patient responses to the presented questions and to store the gathered patient responses in an interview object 926 and a patient demographic dataset 927.

In a particular example embodiment, common statement object option attributes can include the following:

| | |
|---|---|
| Instructions | The instructions presented to the patient to complete the statement. |
| Statement | The question that is presented to the patient during the interview. |
| Sentence | The template used to construct the dictation. The dictation represents the one or more sentences, included in the EMR, which correspond to the patient's answer to the presented question (i.e., the statement). The template is bound to a data set that includes the patient's answer(s) to the statement, the patient data, and the interview state. Using string interpolation and the dynamic nature of the Ruby programming language, the sentence template can access the data bindings and defined macros, which can inject patient-specific and grammatically correct conjugations and gender correct pronouns into an output sentence for inclusion in the EMR 935. For statements that can have more than a single answer, an auto-conjugator option, described in more detail below, defines how a statement will conjugate multiple answers and produce a grammatically correct sentence. |

In a particular example embodiment, statements can be of several different types. These statement types can include: 'STimeAgo', 'SSelect', 'STrueFalse', 'STrueFalseSelect', 'STimeInterval', 'SUserInput', 'SLink', 'SMedicationList', 'SSelectRange', and 'SDietList'. The statement type defines the kind of response expected from a patient in response to statements. For example, the 'STimeAgo' statement type may correspond to a statement such as, "When did you first notice the symptoms." The expected response to this statement would be an indication of time. Given the expected kind of response, an appropriate output sentence or sentence fragment can be associated with the 'STimeAgo' statement type. Similarly, the 'SSelect' statement type may correspond to statements for which a patient is prompted to select from a list of options. The 'STrueFalse' statement type may correspond to statements for which a patient is prompted to provide a "true" or "false" response. The 'STrueFalseSelect' statement type may correspond to statements for which a patient is prompted to provide a "true" or "false" indication per selection response. The 'STimeInterval' statement type may correspond to statements for which a patient is prompted to provide a response corresponding to a time interval. The 'SUserInput' statement type may correspond to statements for which a patient is prompted to provide input corresponding to a particular response. The 'SMedicationList', 'SSelectRange', and 'SDietList' statement types may correspond to statements for which a patient is prompted to provide medication selections, range selections, or diet selections corresponding to particular responses. 'SLink' is a special statement type used to inject additional StatementSets into an output sentence based on patient responses to statements. For each of these statement types, an appropriate output sentence or sentence fragment can be associated with the corresponding statement type.

Generally, the statement object is representative of the use of MSExcel input templates, which can be used to produce MSWord sentences or sentence fragments as described in detail above. In the particular embodiment, the Statement::statement attribute corresponds to the data in the MSExcel input template and Statement::sentence attribute corresponds to the data in the MSWord output document that is automatically generated from the input template.

StatementSet Object

Statements 921 are ordered and grouped into a StatementSet 923. The StatementHTMLBuilder 920 processes the statements of a StatementSet, presents statements to a patient (e.g., the interview process), tracks the state of the interview process, and builds the interview object 926 and patient demographics dataset 927. The ReportBuilder 930 generates the sentences of EMR 935 from the StatementSet(s) 923 and their corresponding Statements 921 by correlating statements to the input provided by the patient during the interview process.

StatementSetProxy Object

StatementSetProxys 922 are used to group a StatementSet 923 into a logical tree, thereby allowing the same StatementSet 923 to be used in multiple positions. StatementSetProxy 922 can be sub-classed allowing section titles to be appropriately named by reflecting the class name. StatementSetProxy 922 can also be used with the FilterFu::Filterable object, described below, thereby allowing age and gender filtering of StatementSets 923.

FilterFu::Filterable Object

Figure 27:
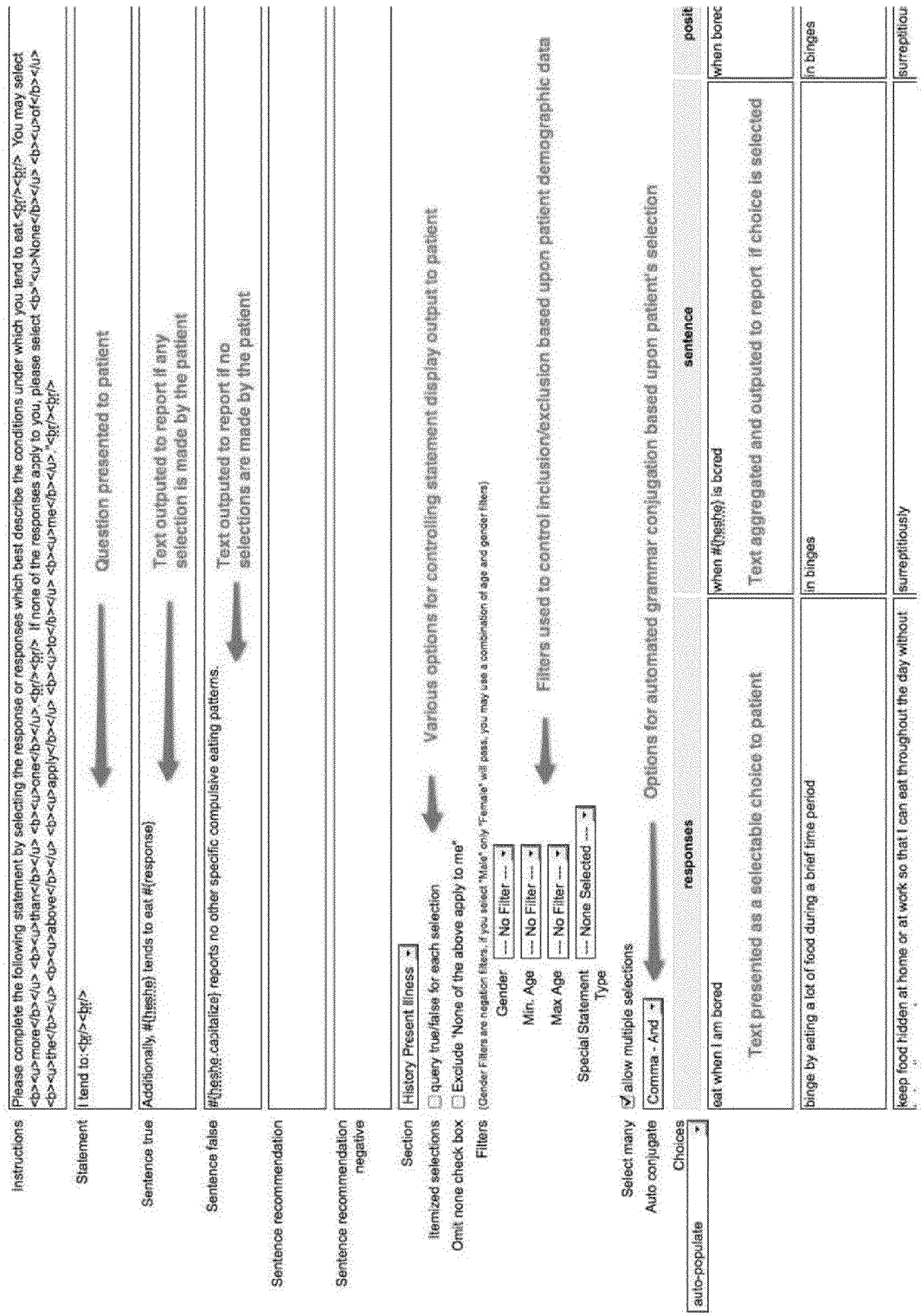
Figure 28:
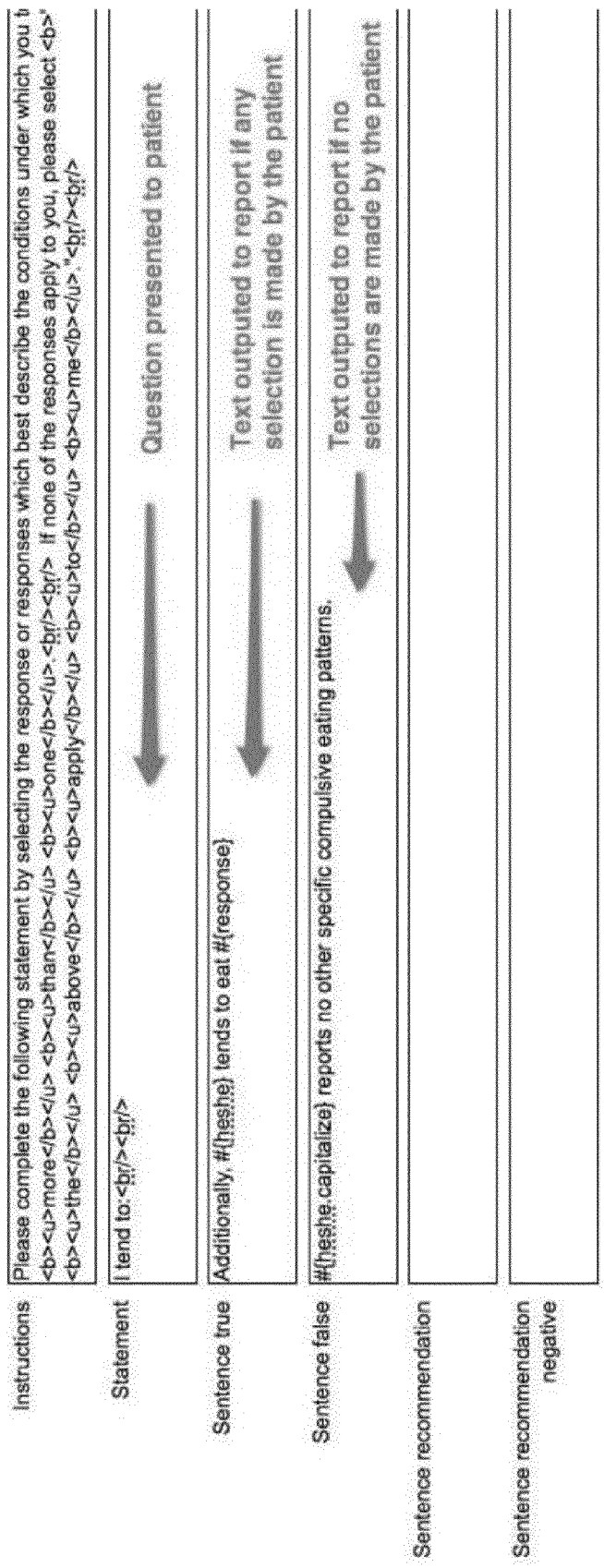
Figure 29:
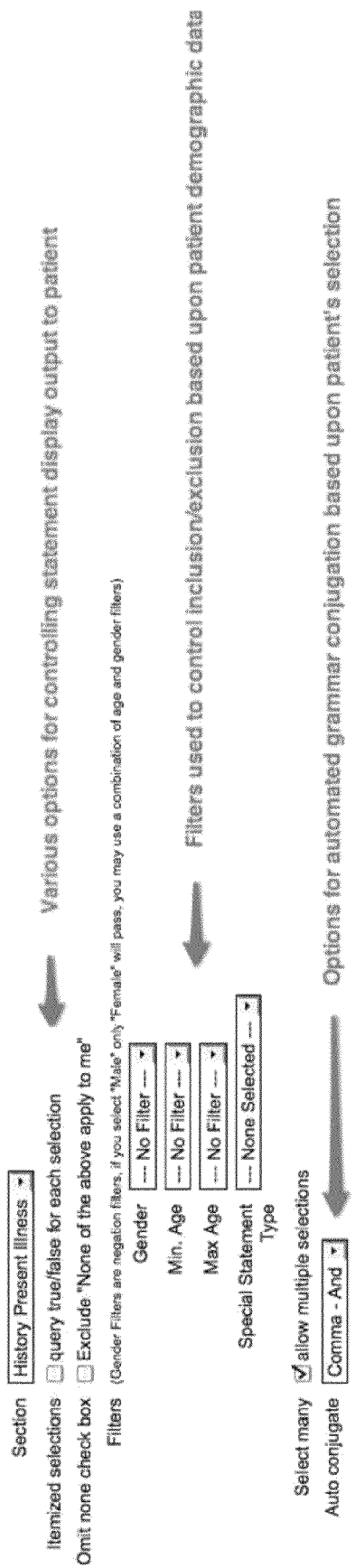

In a particular example embodiment, the processing of statements by the Statement HTML Builder 920 can be further configured using a filtering mechanism. In one embodiment, the filtering mechanism can include the definition of a filter data object used to specify whether particular statements can be filtered (e.g., removed from a particular patient interview session) and if so, how the particular statements are filtered. In a particular example embodiment, a FilterFu::Filterable object can be used to specify whether a particular statement can be filtered. The same object or different objects can also be used to specify a type of filtering. For example, a particular embodiment may allow filtering of statements based on age and/or gender and/or other demographic traits of a particular patient. In general, the FilterFu::Filterable object of an example embodiment allows the logical representation of the configurable type of filtering used on Statements and StatementSetProxys. In a particular embodiment, age and gender filters are supported; but, additional filters can be added. An example of the configurable statement filters of a particular embodiment is shown in the example of FIGS. 27 and 29.

Referring now to FIGS. 26 through 32 as described below, a particular example illustrates the structure and operation of the web application 910 of a particular embodiment. The particular example shown includes screenshots of user interface data displays or views for a user/patient at the Patient site, generated by the Statement HTML Builder 920, in which a patient is shown instructions and a statement and prompted to enter an answer (e.g., see FIG. 26). The particular example shown also includes screenshots of user interface data displays or views for a host administrator at a Back Office site, also generated by the Statement HTML Builder 920, in which a host administrator can configure Statement Sets 923, StatementSetProxies 922, Statements 921, and a set of control options to manipulate the behavior and operation of the web application 910 (e.g., see FIGS. 27-30). Finally, FIGS. 31-32 illustrate a resulting automatically generated patient-specific and grammatically correct EMR 935, which includes a set of patient-specific and grammatically correct sentences generated by the ReportHTMLBuilder 930 based on the configured Statement Sets 923, StatementSetProxies 922, Statements 921, the set of control options, and the data input by the patient. The automatically generated EMR 935 can also include data pulled from the medical database 933. FIGS. 26 through 32, of the particular example, are described in more detail below.

Referring now to FIG. 26, a particular example shows a screenshot of a user interface display or view for a user/patient at the Patient site, generated by the Statement HTML Builder 920. As shown, the screenshot provides instructions to the patient for answering a question as part of a patient interview process. The screenshot also shows the question or query presented to the patient (i.e., "I tend to:"). In relation to the presented question, the screenshot also illustrates a set of suggested answers or response options, which the patient may select using buttons provided by the Patient site user interface 941. In this manner, the patient is prompted to enter an answer for the presented question.

In the particular example shown in FIG. 26, the patient has selected the first three options for the responses that best describe their eating behaviors. It will be apparent to those of ordinary skill in the art that any of the response options could have been selected by the patient. Additionally, the patient could have selected the "None of the above apply to me" option. Once the patient provides a response, the particular response can be saved in the interview object 926 or the patient demographics dataset 927.

As shown in the example of FIG. 26, the patient is generally shown a set of three elements in each step of a patient interview: 1) instructions, 2) a question (denoted a statement), and 3) a set of response options for answering the question. These elements can all be automatically generated and processed using the techniques described herein. In particular, the elements of the example screenshot of FIG. 26 can be generated from and configured using corresponding data objects represented in FIGS. 27 through 30.

Referring now to FIG. 27, a particular example shows a screenshot of a user interface display or view for a host administrator at the Back Office site, generated by the Statement HTML Builder 920. As shown, the screenshot of FIG. 27 provides a view of the data representing the Statement object 921 used to generate the elements of the example screenshot of FIG. 26. The example screenshot of FIG. 27 also includes a view of the data representing the various attributes of the sample Statement object 921. For example, the sample statement object attributes include: 1) instructions (see FIG. 28), 2) a statement corresponding to a question for the patient (see FIG. 28), 3) a set of response options for responding to the statement (see FIG. 30), and 4) a set of sentence or sentence fragment options that correspond to the response options (see FIGS. 28 and 30). The screenshot of FIG. 27 also illustrates a set of configuration options/controls and filters (see FIG. 29) associated with the sample Statement object 921. Using the data and control options specified in the sample Statement object 921 represented in FIG. 27, the Statement HTML Builder 920 can generate the Patient site user interface screen illustrated in FIG. 26 for the particular example. Specifically, the Statement HTML Builder 920 can use the instructions, statement, and response option attributes and the control options of the sample Statement object 921 represented in FIG. 27 to generate the user interface screen illustrated in FIG. 26. It will be apparent to those of ordinary skill in the art that any user interface screen of a patient interview process can be similarly generated by the Statement HTML Builder 920 using properly configured data and control options provided in a statement object 921.

Moreover, the configuration options/controls and filters (see FIG. 29) can be used by the Statement HTML Builder 920 to generate the Patient site user interface screens in a configurable manner. For example, as shown in FIG. 29, an 'Itemized selections' control can be used to specify a true/false query for each selection option in the user interface screen. As shown in FIG. 29, an 'Omit none check box' control can be used to specify the inclusion or exclusion of a "None of the above apply to me" response option in the user interface screen. As shown in FIG. 29, various Filter controls can be used to specify the inclusion or exclusion of particular statements based on demographic characteristics of a particular patient being interviewed. In one embodiment, these filters can include gender and age filters. As shown in FIG. 29, a 'Special statement type' control can be used to specify the type of statement. The statement types are described in detail above. As also shown in FIG. 29, a 'Select many' control can be used to specify whether the patient can provide only a single response or a plurality of responses to the presented statement. It will be apparent to those of ordinary skill in the art that other control options and/or filters can be similarly provided to configure the operation of the Statement HTML Builder 920.

The Report HTML Builder 930 can use the data and control options specified in the sample Statement object 921 represented in FIG. 27 along with data retained in the interview object 926, patient demographics dataset 927, and medical database 933 to generate the patient-specific and grammatically correct electronic medical record (EMIR) 935 illustrated in FIGS. 31 and 32 for a particular example. Specifically, the Report HTML Builder 930 can use the particular responses provided by the patient as saved in the interview object 926 and the patient demographics dataset 927 to retrieve the appropriate sentences or sentence fragments that correspond to the particular patient responses (see FIGS. 28 and 30). These retrieved sentences or sentence fragments can be merged into or appended to the corresponding EMR 935 (see FIGS. 31-32).

Moreover, the configuration options/controls and filters (see FIG. 29) can be used by the Report HTML Builder 930 to generate the EMR 935 in a configurable manner. For example, as shown in FIG. 29, a 'Section' control can be used to specify a particular portion of an EMR 935 in which the retrieved sentences or sentence fragments can be merged into the corresponding EMR 935. As also shown in FIG. 29, an 'Auto-conjugate' control can be used to specify a configurable manner for handling multiple responses. In particular, the 'Auto-conjugate' control allows the Report HTML Builder 930 to automatically separate, in a grammatically correct way, the indeterminate number of responses from a patient to a Statement. In a particular embodiment, the 'Auto-conjugate' options include: "Comma And", "Comma Or" and "Semicolon". For example, a particular statement may query the patient to, "Select all of the parts of your body that hurt." In response to this statement, the patient may answer in a variety of ways as follows.

If the patient responds with just "Head", the Report HTML Builder 930 generates just "Head" and the auto-conjugator does nothing.

If the patient responds with "Head, Feet", then the Report HTML Builder 930 generates one of the following configurable outputs:
with the auto-conjugate control set to "Comma And", the Report HTML Builder 930 generates the output: "Head and Feet".
with the auto-conjugate control set to "Comma Or" the Report HTML Builder 930 generates the output: "Head or Feet"

with the auto-conjugate control set to "Semicolon" the Report HTML Builder 930 generates the output: "Head; Feet"

If the patient responds with "Head, Neck, Feet" then the Report HTML Builder 930 generates one of the following configurable outputs:
with the auto-conjugate control set to "Comma And" the Report HTML Builder 930 generates the output: "Head, Neck and Feet"
with the auto-conjugate control set to "Comma Or" the Report HTML Builder 930 generates the output: "Head, Neck or Feet"
with the auto-conjugate control set to "Semicolon" the Report HTML Builder 930 generates the output: "Head; Neck; Feet"

It will be apparent to those of ordinary skill in the art that other control options can be similarly provided to configure the operation of the Report HTML Builder 930.

Figure 33:
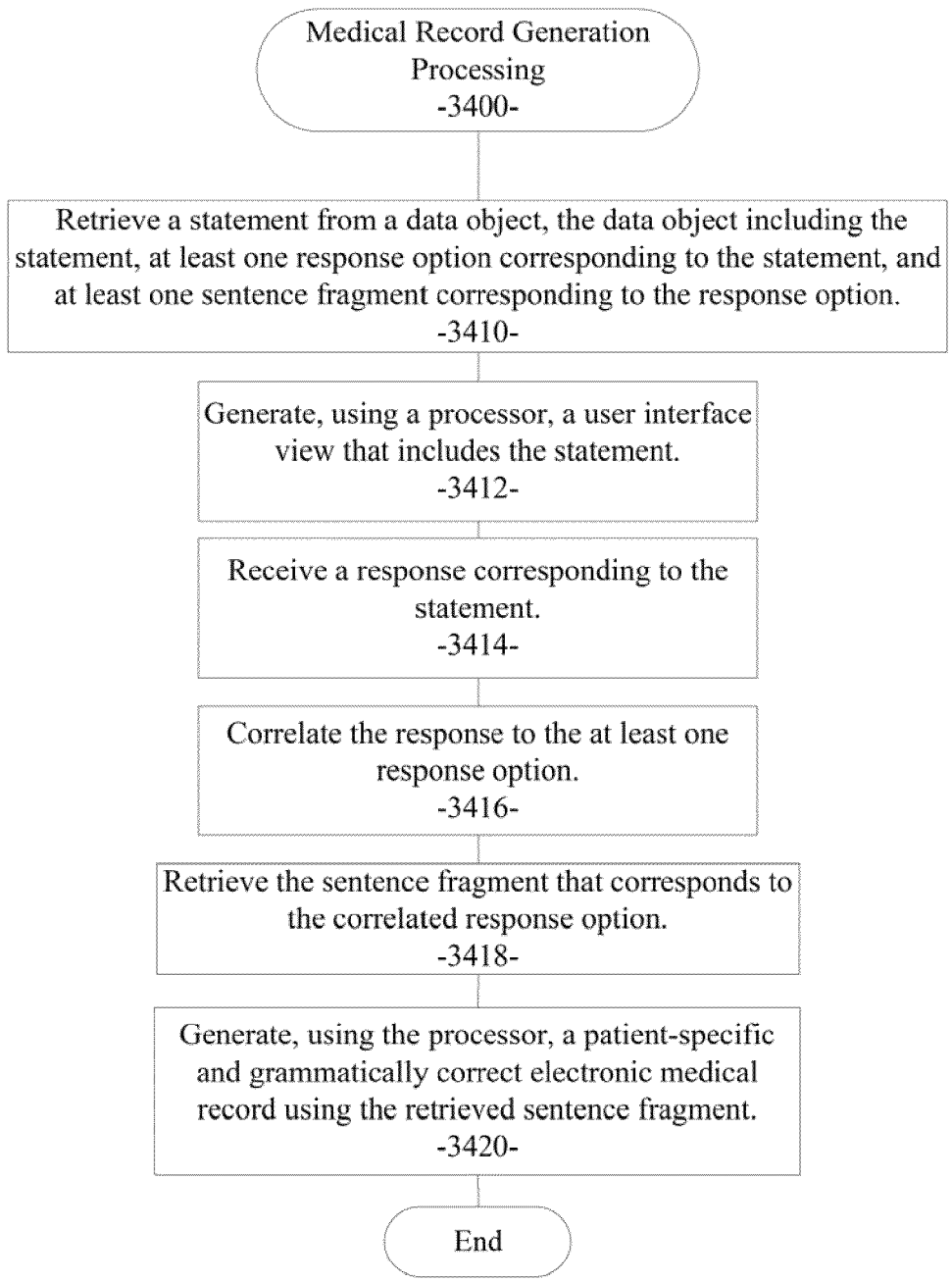
FIG. 33 is a flow diagram illustrating a processing flow in a particular embodiment.

Referring now to FIG. 33, a flow diagram illustrates a processing flow in a particular embodiment. As illustrated, the method in a particular embodiment includes: retrieving a statement from a data object, the data object including the statement, at least one response option corresponding to the statement, and at least one sentence fragment corresponding to the response option (processing block 3410); generating, using a processor, a user interface view that includes the statement (processing block 3412); receiving a response corresponding to the statement (processing block 3414); correlating the response to the at least one response option (processing block 3416); retrieving the sentence fragment that corresponds to the correlated response option (processing block 3418); and generating, using the processor, a patient-specific and grammatically correct electronic medical record using the retrieved sentence fragment (processing block 3420).

Thus, as described above, a system and method for automatically generating patient-specific and grammatically correct electronic medical records is disclosed. Although the disclosed subject matter has been described with reference to several example embodiments, it may be understood that the words that have been used are words of description and illustration, rather than words of limitation. Changes may be made within the purview of the appended claims, as presently stated and as amended, without departing from the scope and spirit of the disclosed subject matter in all its aspects. Although the disclosed subject matter has been described with reference to particular means, materials, and embodiments, the disclosed subject matter is not intended to be limited to the particulars disclosed; rather, the subject matter extends to all functionally equivalent structures, methods, and uses such as are within the scope of the appended claims.

What is claimed is:

1. A method comprising:
generating a data object including a plurality of statements, a plurality of response options corresponding to each statement, and mapping data that maps each of the plurality of response options to at least one corresponding sentence fragment, text content of the plurality of response options being different than text content of a corresponding sentence fragment, at least one response option of the plurality of response options being mapped to a plurality of corresponding sentence fragments, the mapping data further including, for each of the plurality of response options, data that maps a particular response option to a corresponding specific location in an electronic medical record, the specific location being individually pre-defined for each of the plurality of response options, at least one response option of the plurality of response options being mapped to a plurality of corresponding specific locations in the electronic medical record, the data object further including, for each of the plurality of response options, a link target specifying a set of follow-on queries that relate to a particular response option, the follow-on queries only being presented to a user if the corresponding response option is selected;

retrieving a statement from the data object;

generating, using a processor, a user interface view that includes the statement;

receiving a response corresponding to the statement;

correlating the response to a chosen one of the plurality of response options;

mapping, using the processor, the chosen response option to one or more corresponding sentence fragments using the mapping data in the data object;

retrieving the one or more mapped sentence fragments to which the chosen response option is mapped;

identifying, using the processor, a specific location in the electronic medical record corresponding to the chosen response option using the mapping data in the data object;

placing the one or more mapped sentence fragments into the electronic medical record at the specific location;

retrieving patient demographic information for insertion into the electronic medical record;

placing the patient demographic information into the electronic medical record at a pre-defined location; and generating, using the processor, the patient-specific and grammatically correct electronic medical record using the one or more mapped sentence fragments and the patient demographic information.

2. The method as claimed in claim 1 further including providing a set of control options for configuring the generation of the user interface view.

3. The method as claimed in claim 1 wherein the response is received via a website user interface.

4. The method as claimed in claim 1 wherein the response is received from a patient.

5. The method as claimed in claim 1 further including retrieving medical data from a medical database.

6. The method as claimed in claim 1 wherein the electronic medical record is one or more of: a medical history, a surgical record, a mental health record, hospital record, counseling record, coaching record, physical therapy record, mental therapy record, and behavioral therapy record.

7. The method as claimed in claim 1 further including an auto-conjugate control option.

8. The method as claimed in claim 1 further including a filtering control option.

9. A system comprising:

a processor;

a memory coupled to the processor to store information related to electronic medical records, the memory including a data object including a plurality of statements, a plurality of response options corresponding to each statement, and mapping data that maps each of the plurality of response options to at least one corresponding sentence fragment, text content of the plurality of response options being different than text content of a corresponding sentence fragment, at least one response option of the plurality of response options being mapped to a plurality of corresponding sentence fragments, the mapping data further including, for each of the plurality of response options, data that maps a particular response option to a corresponding specific location in an electronic medical record, the specific location being individually pre-defined for each of the plurality of response options, at least one response option of the plurality of response options being mapped to a plurality of corresponding specific locations in the electronic medical record, the data object further including, for each of the plurality of response options, a link target specifying a set of follow-on queries that relate to a particular response option, the follow-on queries only being presented to a user if the corresponding response option is selected;

an input component to retrieve a statement from the data object; to generate a user interface view that includes the statement; to receive a response corresponding to the statement; and to correlate the response to a chosen one of the plurality of response options; and an output component to map the chosen response option to one or more corresponding sentence fragments using the mapping data in the data object; response option being different than text content of the one or more sentence fragments to to retrieve the one or more mapped sentence fragments to which the chosen response option is mapped; to identify a specific location in the electronic medical record corresponding to the chosen response option using the mapping data in the data object; to place the one or more mapped sentence fragments into the electronic medical record at the specific location; to retrieve patient demographic information for insertion into the electronic medical record; to place the patient demographic information into the electronic medical record at a pre-defined location; and to generate the patient-specific and grammatically correct electronic medical record using the one or more mapped sentence fragments and the patient demographic information.

10. The system as claimed in claim 9 being further configured to provide a set of control options for configuring the generation of the user interface view.

11. The system as claimed in claim 9 wherein the response is received via a website user interface.

12. The system as claimed in claim 9 wherein the response is received from a patient.

13. The system as claimed in claim 9 being further configured to retrieve medical data from a medical database.

14. The system as claimed in claim 9 wherein the electronic medical record is one or more of: a medical history, a surgical record, a mental health record, hospital record, counseling record, coaching record, physical therapy record, mental therapy record, and behavioral therapy record.

15. The system as claimed in claim 9 being further configured to provide an auto-conjugate control option.

16. The system as claimed in claim 9 being further configured to provide a filtering control option.

17. An article of manufacture comprising a non-transitory machine-readable medium having machine executable instructions embedded thereon, which when executed by a machine, cause the machine to:

generate a data object including a plurality of statements, a plurality of response options corresponding to each statement, and mapping data that maps each of the plurality of response options to at least one corresponding sentence fragment, text content of the plurality of response options being different than text content of a corresponding sentence fragment, at least one response option of the plurality of response options being mapped to a plurality of corresponding sentence fragments, the mapping data further including, for each of the plurality of response options, data that maps a particular response option to a corresponding specific location in an electronic medical record, the specific location being individually pre-defined for each of the plurality of response options, at least one response option of the plurality of response options being mapped to a plurality of corresponding specific locations in the electronic medical record, the data object further including, for each of the plurality of response options, a link target specifying a set of follow-on queries that relate to a particular response option, the follow-on queries only being presented to a user if the corresponding response option is selected;

retrieve a statement from the data object;

generate, using a processor, a user interface view that includes the statement;

receive a response corresponding to the statement;

correlate the response to a chosen one of the plurality of response options;

map the chosen response option to one or more corresponding sentence fragments using the mapping data in the data object;

retrieve the one or more mapped sentence fragments to which the chosen response option is mapped;

identify a specific location in the electronic medical record corresponding to the chosen response option using the mapping data in the data object;

place the one or more mapped sentence fragments into the electronic medical record at the specific location;

retrieve patient demographic information for insertion into the electronic medical record;

place the patient demographic information into the electronic medical record at a pre-defined location; and generate, using the processor, the patient-specific and grammatically correct electronic medical record using the one or more mapped sentence fragments and the patient demographic information.

* * * * *